US012336911B2

(12) United States Patent
Harmon et al.

(10) Patent No.: US 12,336,911 B2
(45) Date of Patent: Jun. 24, 2025

(54) ORTHOPEDIC IMPLANTS AND METHODS

(71) Applicant: Smith & Nephew, Inc., Memphis, TN (US)

(72) Inventors: Jon A. Harmon, Byhalia, MS (US); Ruxandra C. Marinescu Tanasoca, Memphis, TN (US); Ryan Landon, Olive Branch, MS (US); Mark Housman, North Attleboro, MA (US); Sean Haddock, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 502 days.

(21) Appl. No.: 16/650,239

(22) PCT Filed: Oct. 26, 2018

(86) PCT No.: PCT/US2018/057654
§ 371 (c)(1),
(2) Date: Mar. 24, 2020

(87) PCT Pub. No.: WO2019/084363
PCT Pub. Date: May 2, 2019

(65) Prior Publication Data
US 2020/0306050 A1    Oct. 1, 2020

Related U.S. Application Data

(60) Provisional application No. 62/577,205, filed on Oct. 26, 2017.

(51) Int. Cl.
*A61F 2/38* (2006.01)
*A61F 2/30* (2006.01)

(52) U.S. Cl.
CPC ...... *A61F 2/389* (2013.01); *A61F 2002/3082* (2013.01); *A61F 2002/30841* (2013.01);
(Continued)

(58) Field of Classification Search
None
See application file for complete search history.

(56) References Cited

U.S. PATENT DOCUMENTS 5,480,445 A * 1/1996 Burkinshaw ............ A61F 2/389
623/20.32
5,609,641 A * 3/1997 Johnson .................. A61F 2/389
623/20.32

(Continued)

FOREIGN PATENT DOCUMENTS

FR        2674124 A1    3/1991

OTHER PUBLICATIONS

International Search Report and Written Opinion for International Patent Application No. PCT/US2018/057654, mailed Apr. 1, 2019.
(Continued)

*Primary Examiner* — Megan Y Wolf
(74) *Attorney, Agent, or Firm* — KDW Firm PLLC

(57) ABSTRACT

There is provided a tibial component comprising a tibial tray having a superior side and an inferior side, and a support member connected to the inferior side of the tibial tray, the support member having a stem portion, the stem portion including one or more fins and a first arm angled relative to a second arm. In one form, the fins have a curvature that extends away from the stem portion. In another form, the first arm defines an opening sized to receive an anchor wherein the anchor is configured to penetrate a portion of bone and the opening in the first arm. Optionally, the stem portion includes a first portion having a first cross sectional area and a second portion having a second cross sectional area wherein the first cross sectional area is larger than the second cross sectional area. The fins and arms can include rail protrusions.

15 Claims, 23 Drawing Sheets

(52) U.S. Cl.
CPC .............. *A61F 2002/30845* (2013.01); *A61F 2002/30878* (2013.01); *A61F 2002/30879* (2013.01); *A61F 2002/30884* (2013.01)

(56) References Cited

U.S. PATENT DOCUMENTS

| | | |
|---|---|---|
| 5,658,341 A | 8/1997 | Delfosse |
| 2006/0116772 A1 | 6/2006 | Haidukewych |
| 2007/0203582 A1 | 8/2007 | Campbell et al. |
| 2009/0265011 A1* | 10/2009 | Mandell .............. A61F 2/30734 606/88 |
| 2012/0041564 A1 | 2/2012 | Lloyd et al. |
| 2013/0310948 A1 | 11/2013 | Luscher |
| 2014/0257507 A1* | 9/2014 | Wang ...................... A61F 2/461 623/20.34 |
| 2016/0278929 A1 | 9/2016 | Harris et al. |

OTHER PUBLICATIONS

European Search Report, European Patent Office, 7 Pages, Nov. 15, 2023.

\* cited by examiner

ORTHOPEDIC IMPLANTS AND METHODS

CROSS-REFERENCE TO RELATED APPLICATION

The present application is a United States National Phase filing of International Application No. PCT/US2018/057654, filed Oct. 26, 2018, which claims the benefit of the filing date of U.S. Provisional Application No. 62/577,205 filed on Oct. 26, 2017, which applications are expressly incorporated herein by reference.

TECHNICAL FIELD

The present disclosure generally relates to orthopedic implants and methods involving the same, such as, but not limited to, orthopedic implants and methods for the proximal tibia, such as tibial components, and more particularly but not exclusively relates to tibial components and fixation of those tibial components to bone.

BACKGROUND

There are several factors that are potentially relevant to the design and performance of orthopedic implants. In the example of a tibial tray, a non-exhaustive list of such factors includes the implant's flexibility (or the flexibility of certain portions of the implant or its flexibility about certain axes or other constructs), which may indicate the degree to which the tray conforms to the potentially uneven resected surfaces of a proximal tibia; the implant's rigidity (or the rigidity of certain portions of the implant or its rigidity about certain axes or other constructs), which may indicate the degree to which stresses or other forces imposed by the bony and other anatomy associated with the knee joint are transmitted to the peripheral hard cortical shell of the proximal tibia; the implant's resistance to rotation; the amount of bone preserved; and/or other potentially relevant factors. In some instances, accommodation of these or other factors may require trade-offs to balance competing factors. In some instances, one or more of these factors may not be considered or given a high level of importance to the design of an orthopedic implant.

Tibial trays can be attached to bone with the use of bone cement for immediate fixation in a patient. Although cemented tibial trays have immediate fixation in a patient, the use of bone cement has many drawbacks and side effects that have led to the development of cementless knee implants, including tibial trays. Cementless tibial trays can be attached to bone within a patient without the use of bone cement. Although these cementless tibial trays obviate the need for bone cement and the associated concerns with bone cement within a patient, cementless tibial trays have disadvantages as well.

One challenge for cementless tibial trays is a low amount of fixation between the tibial tray and bone post-operatively, because the bonding between the tibial tray and the bone is dependent on bone ingrowth. This situation leads to a lack of immediate postoperative stability. Another challenge for cementless tibial trays is it can be several months before ingrowth occurs, such that the interim period can place the patient at risk with less than ideal implant stability, knee pain, increased risk of loosening of the implant and/or failure of the implant.

For these reasons among others, a need remains for further improvements in this technological field.

SUMMARY

A tibial component comprising a tibial tray having a superior side and an inferior side, and a support member connected to the inferior side of the tibial tray, the support member having a stem portion, the stem portion including one or more fins and a first arm angled relative to a second arm. Some of the non-limiting embodiments of tibial components described herein include one or more fins or keels that include or define holes, openings, recesses, ridges or protrusions, curvature of fins, coatings or antibacterial carriers on the trays, support members, and fasteners, fasteners for attachment of the support member, fins, or arms to bone, or other structures or features. Some of the non-limiting embodiments of tibial components described herein may additionally or alternatively include a monolithic, modular or otherwise connected stem or support member to the tibial trays. The present application is not limited to tibial components; however, and one of skill in the art will recognize that at least some of the concepts presented herein could be applied to other orthopedic implants.

There is provided a tibial component comprising a tibial tray having a superior side and an inferior side, and a support member connected to the inferior side of the tibial tray, the support member having a stem portion, the stem portion including one or more fins and a first arm angled relative to a second arm, wherein the one or more fins are sized differently than the first arm and the second arm.

According to some embodiments, the first arm and the second arm each have a length that is between 0.20 to 0.80 of the length of the one or more fins as measured along a longitudinal axis of the stem portion.

According to some embodiments, the one or more fins each have a curvature that extends away from a rim of the tibial tray.

According to some embodiments, the one or more fins each have a curvature that extends towards the support member.

According to some embodiments, the one or more fins are spaced equally around the stem portion.

According to some embodiments, a first one of the fins forms an angle with a second one of the fins, wherein the angle is between about 20 degrees to about 180 degrees.

According to some embodiments, the angle is between about 120 degrees to about 130 degrees.

According to some embodiments, the first arm defines an opening sized to receive an anchor.

According to some embodiments, an anchor configured to penetrate a portion of bone and the opening in the first arm.

According to some embodiments, the anchor includes a rib on an outer surface.

According to some embodiments, the anchor includes a plurality of lateral ribs that span around an outer surface of the anchor and a plurality of longitudinal barbs that span along a length of the anchor.

According to some embodiments, the longitudinal barbs are arranged in an alternating relationship with the lateral ribs.

According to some embodiments, the stem portion includes a first portion adjacent the inferior side of the tibial tray and a second portion that extends away from the first portion, the first portion has a first cross sectional area and the second portion has a second cross sectional area wherein the first cross sectional area is larger than the second cross sectional area.

According to some embodiments, the stem portion has a cross sectional area that forms a tear drop shape. According to some embodiments, the stem portion has a cross sectional area that forms two connected generally cylindrical faces.

According to some embodiments, the one or more fins each include one or more rail protrusions.

According to some embodiments, the first arm and the second arm each include one or more rail protrusions.

According to some embodiments, the one or more rail protrusions extend along a length of the one or more fins or the first and second arms.

According to some embodiments, the one or more rail protrusions are spaced along the one or more fins or the first and second arms in a uniform spacing arrangement.

According to some embodiments, the one or more rail protrusions are spaced along the one or more fins or the first and second arms in a non-uniform spacing arrangement.

According to some embodiments, the one or more fins have a length that extends from the inferior side of the tibial tray to a location on the stem portion that is between about 0.5 and 0.90 of the length of the stem portion. According to some embodiments, the one or more fins have a length that extends from the inferior side of the tibial tray to a location on the stem portion that is between 0.05 and 0.90 of the length of the stem portion, and more particularly between 0.5 and 0.90 of the length of the stem portion.

According to some embodiments, the one or more fins includes at least two fins, the stem portion includes a groove positioned between the two fins.

According to some embodiments, the groove spans longer than the two fins.

According to some embodiments, further comprises one or more pegs attached to the inferior side of the tibial tray.

According to some embodiments, the first arm has a first curvature that extends away from the stem portion and the second arm has a second curvature that extends away from the stem portion.

According to some embodiments, the tibial tray defines a notch.

Beneficially, the fins and/or arm provide more rotational resistance and strength for the tibial component when it is implanted. The unique configuration of fins, arms, and support member improve fixation between the tibial tray and bone post-operatively. The features of the tibial components described herein correspond to different features of the bone at a variety of cross sectional shapes. Similarly, the unique arrangement and configuration of these components in tibial components provide similar benefits and other benefits as described below.

Another embodiment of the tibial component can include the addition of a fixation screw or anchor to the distal side of the tibial component. Traditional screw fixation on tibial trays is from the superior to inferior direction and through the tibial tray itself, thus anchoring the tibial tray down to the plateau. As disclosed herein, screws or anchors can enter in an anterior to posterior direction, and lock on to the tibial component within the fin itself or other distally placed feature, thus anchoring the tibial component to the proximal tibia. The screws or anchors can be permanent or temporary, and may be resorbable. Examples of anchors or screws are illustrated in FIGS. 12-20. The anchors can be an optional feature, a decision to be made intraoperatively if it was found that the bone quality was not sufficient to support a cementless application of the tibial component, or if a user was not pleased with the degree of initial fixation that he/she was experiencing in a porous case.

Further features and advantages of at least some of the embodiments of the present invention, as well as the structure and operation of various embodiments of the present invention, are described in detail below with reference to the accompanying drawings.

DETAILED DESCRIPTION OF ILLUSTRATIVE EMBODIMENTS

Figure 1:
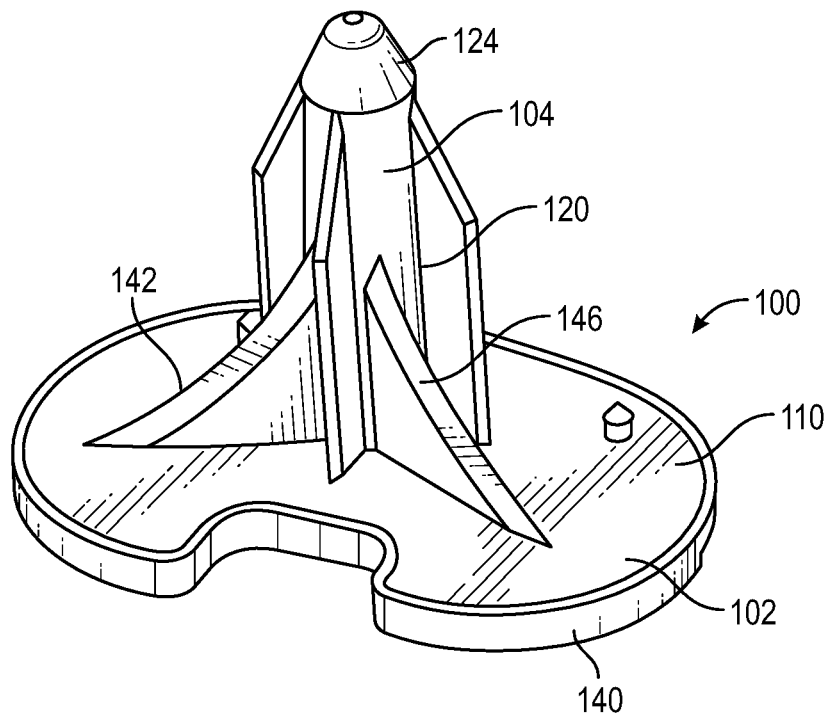
FIG. 1 is a perspective view of a tibial component according to one embodiment.
Figure 2:
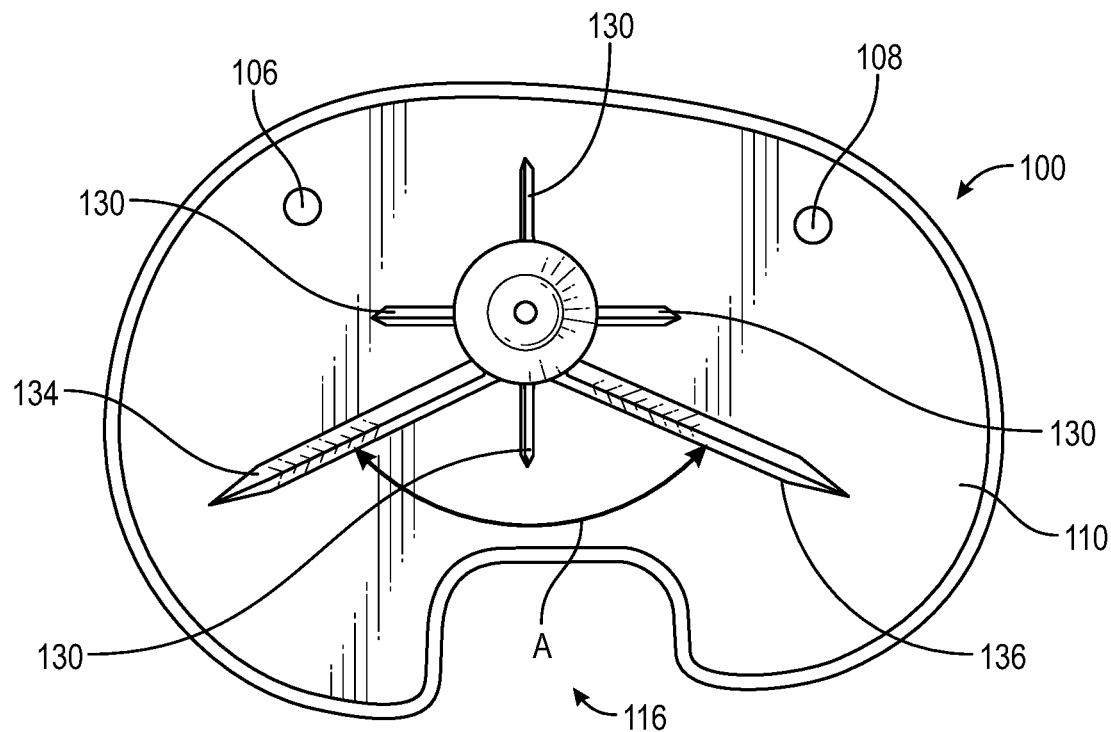
FIG. 2 is a top view of the tibial component illustrated in FIG. 1.
Figure 3:
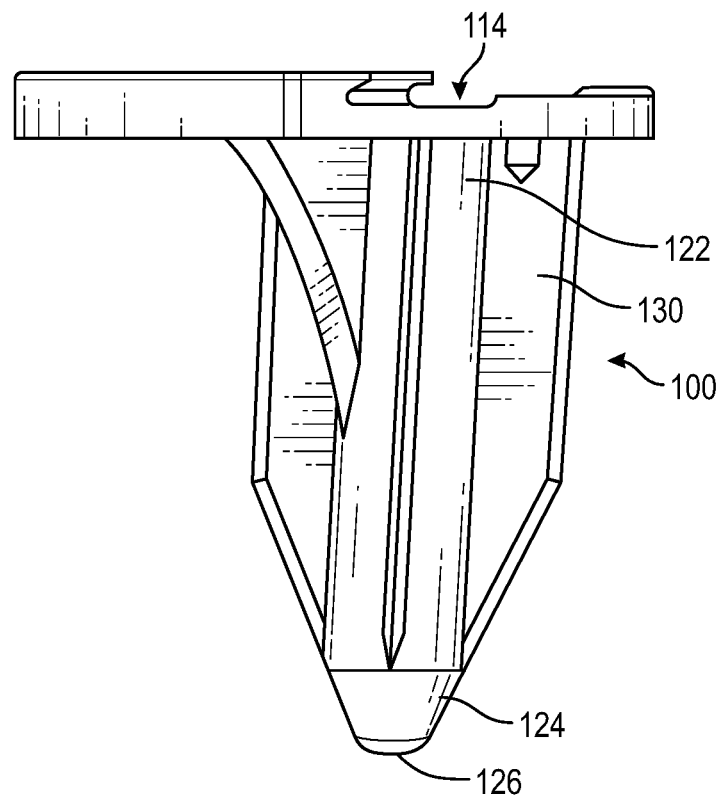
FIG. 3 is a medial-lateral view of the tibial component illustrated in FIG. 1
Figure 4:
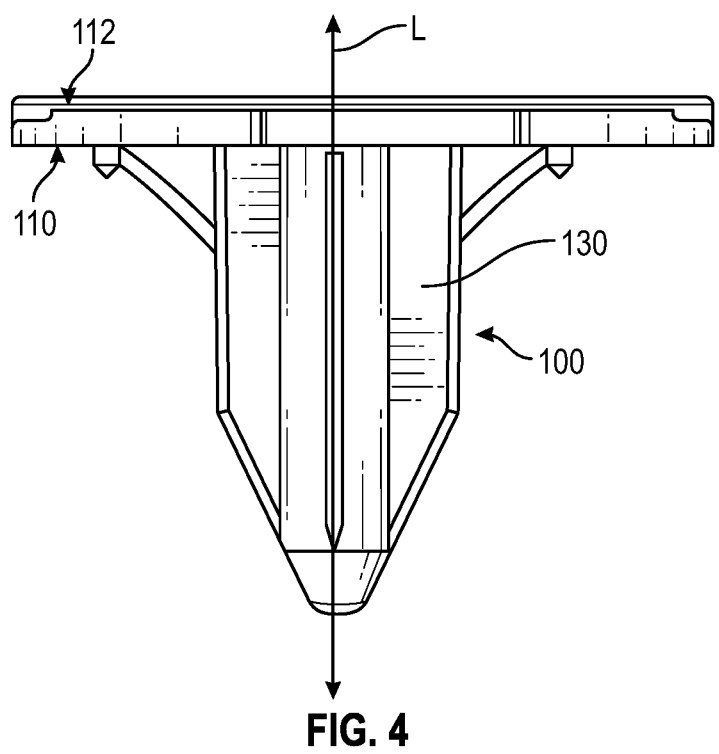
FIG. 4 is an anterior-posterior view of the tibial component illustrated in FIG. 1.
Figure 5:
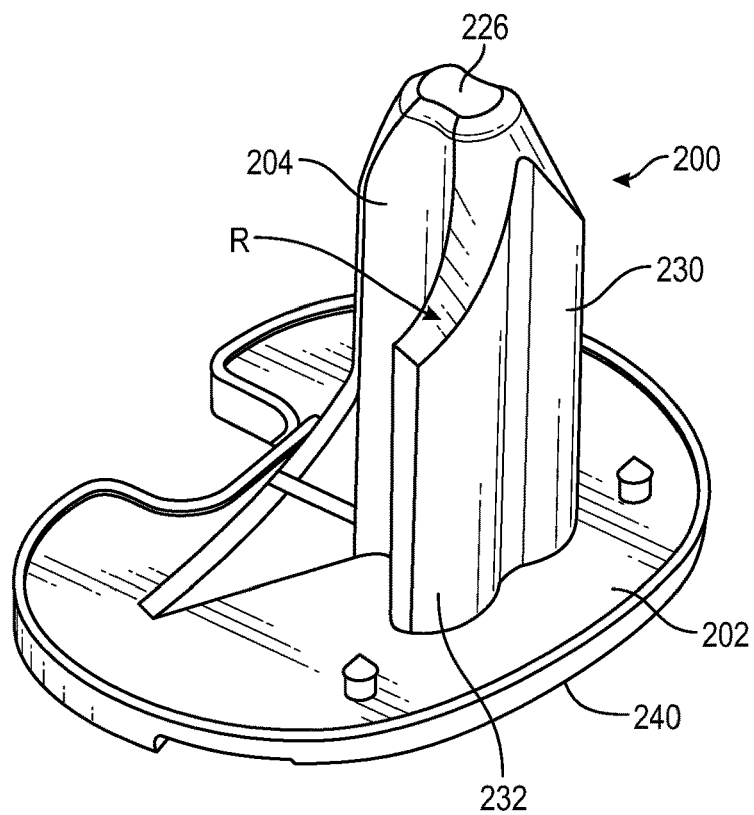
FIG. 5 is a perspective view of a tibial component according to second embodiment.
Figure 6:
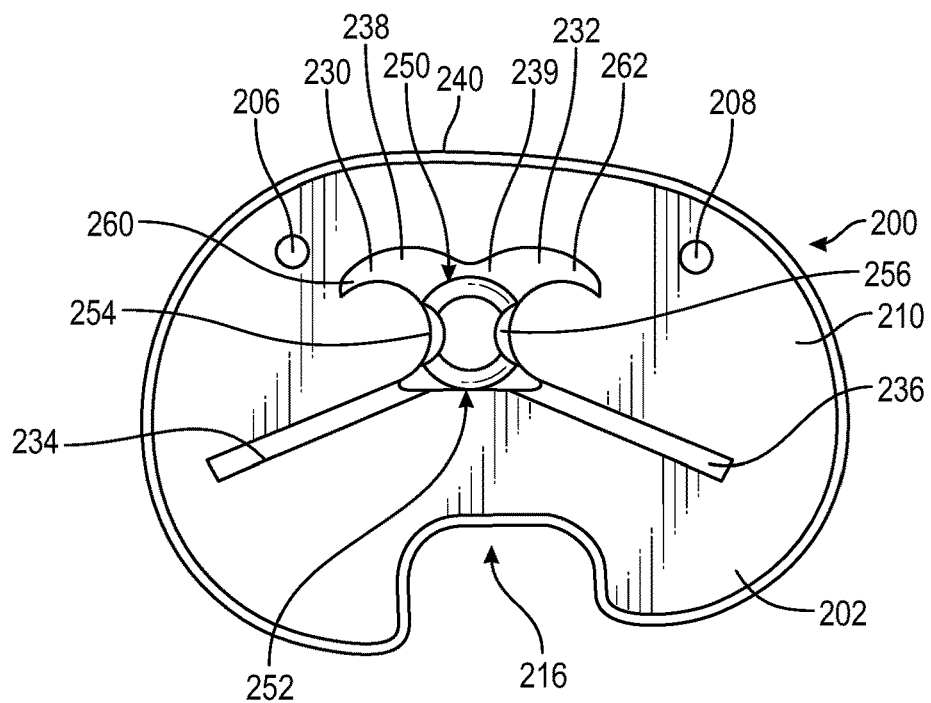
FIG. 6 is a top view of the tibial component illustrated in FIG. 5.
Figure 7:
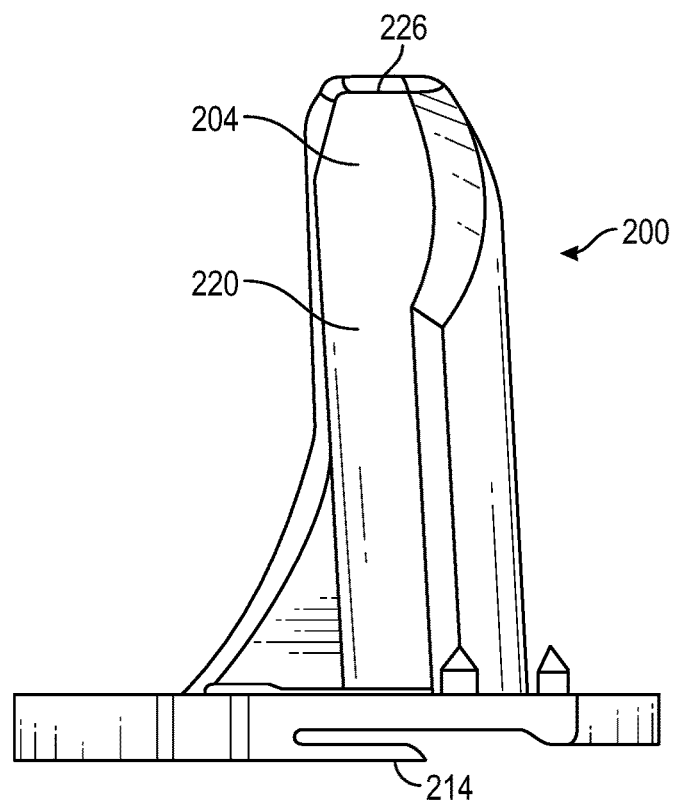
FIG. 7 is a side view of the tibial component illustrated in FIG. 5.
Figure 8:
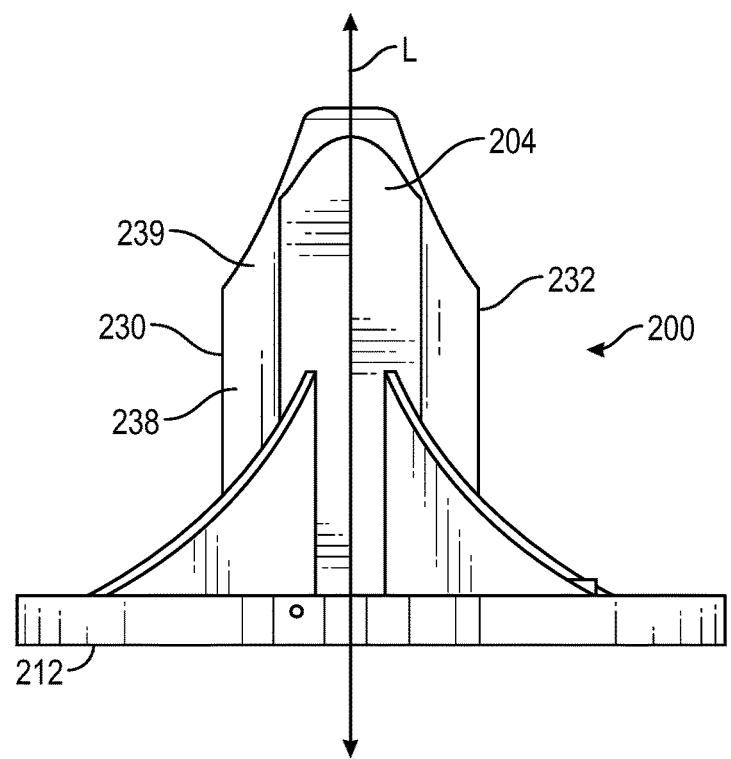
FIG. 8 is a rear view of the tibial component illustrated in FIG. 5.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 9:
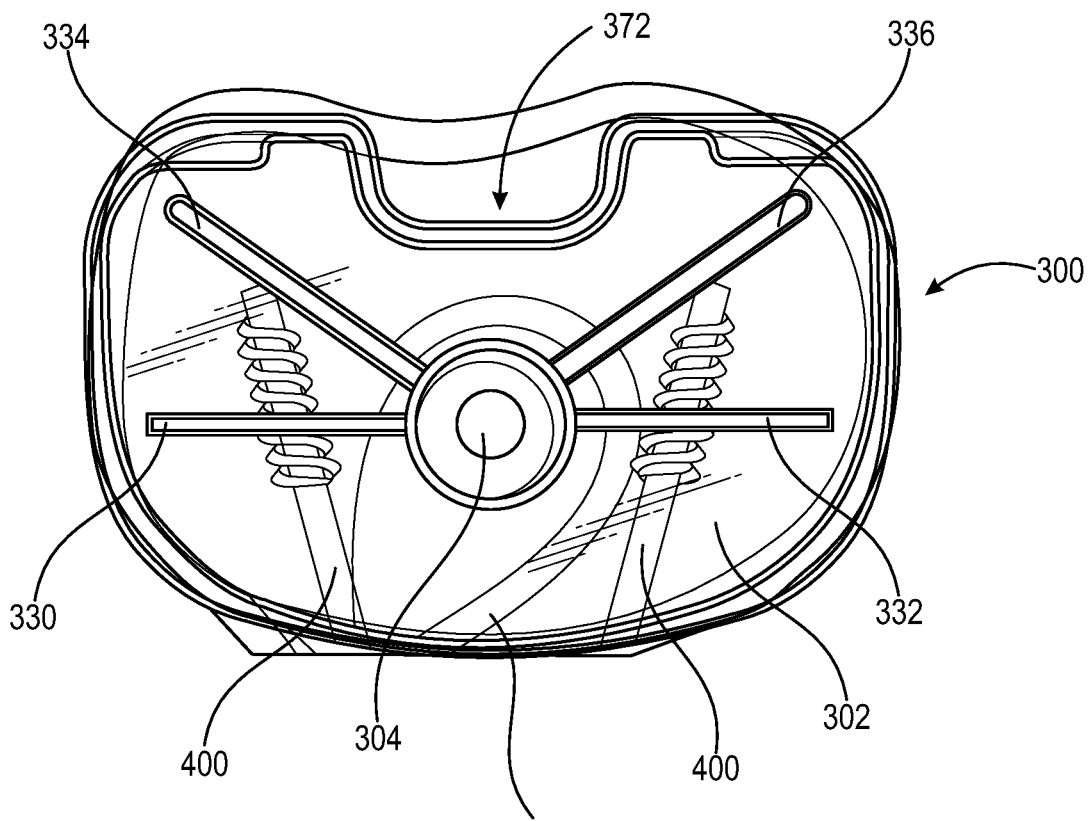
FIG. 9 is a top view of a tibial component according to a third embodiment implanted in bone.
Figure 10:
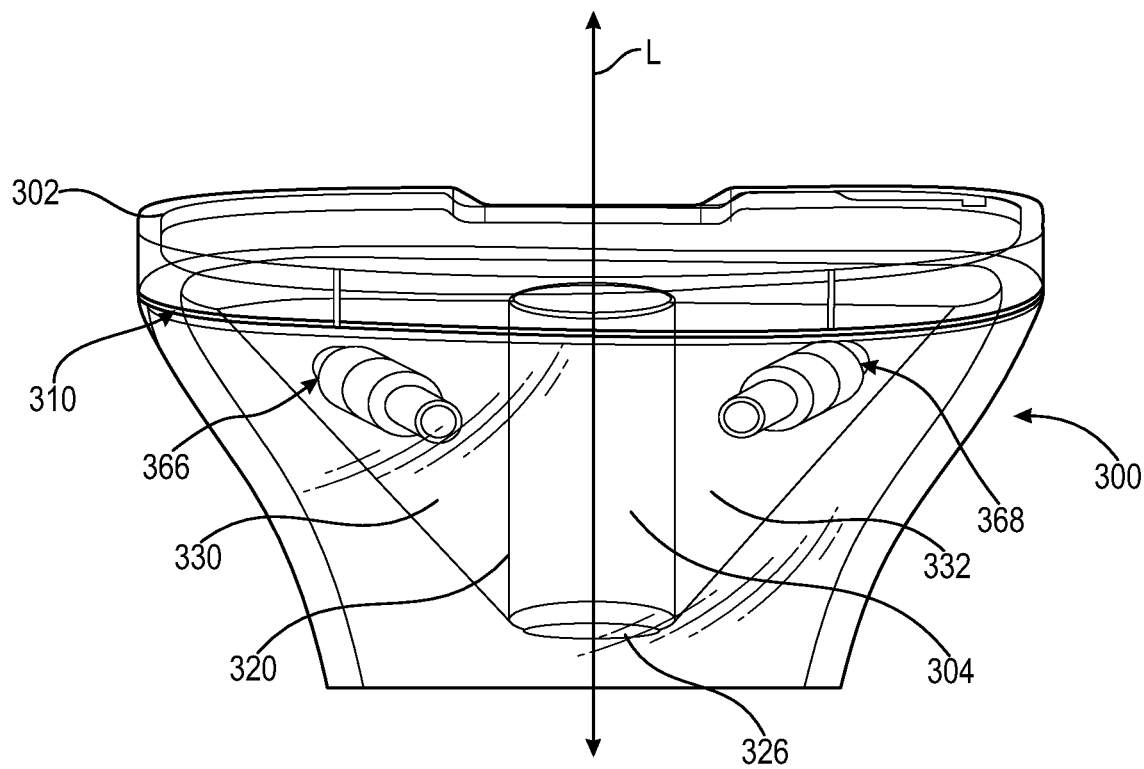
FIG. 10 is a rear view of the tibial component illustrated in FIG. 9.
Figure 11:
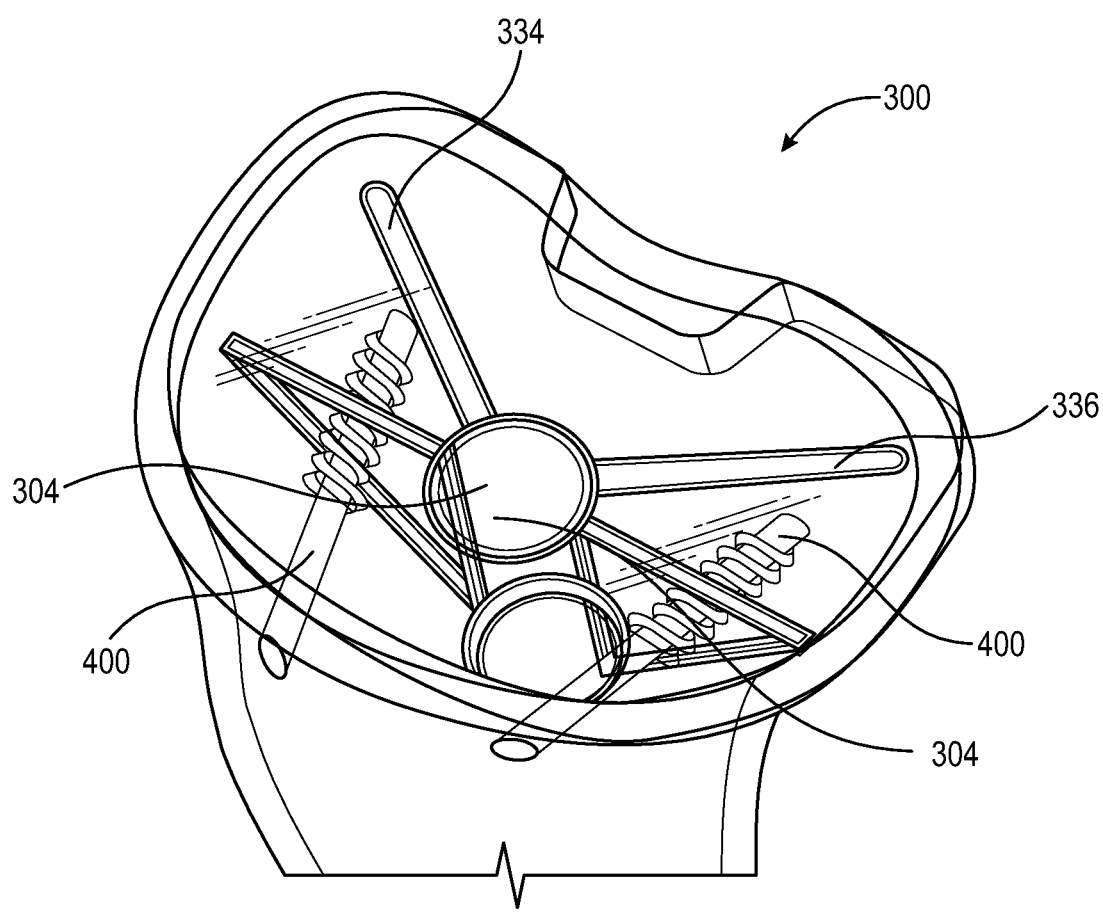
FIG. 11 is a perspective view of a tibial component illustrated in FIG. 9.
Figure 27:
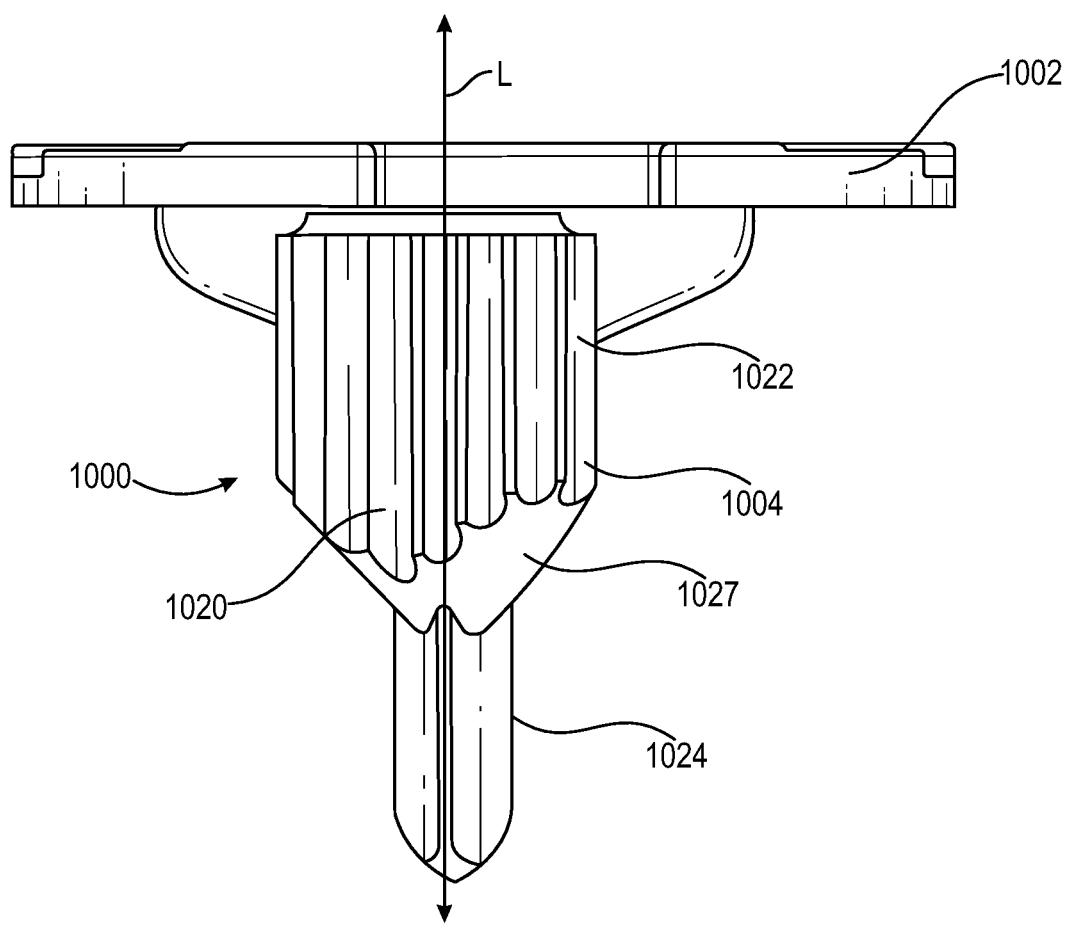
FIG. 27 is a rear view of a tibial component according to a fifth embodiment.
Figure 28:
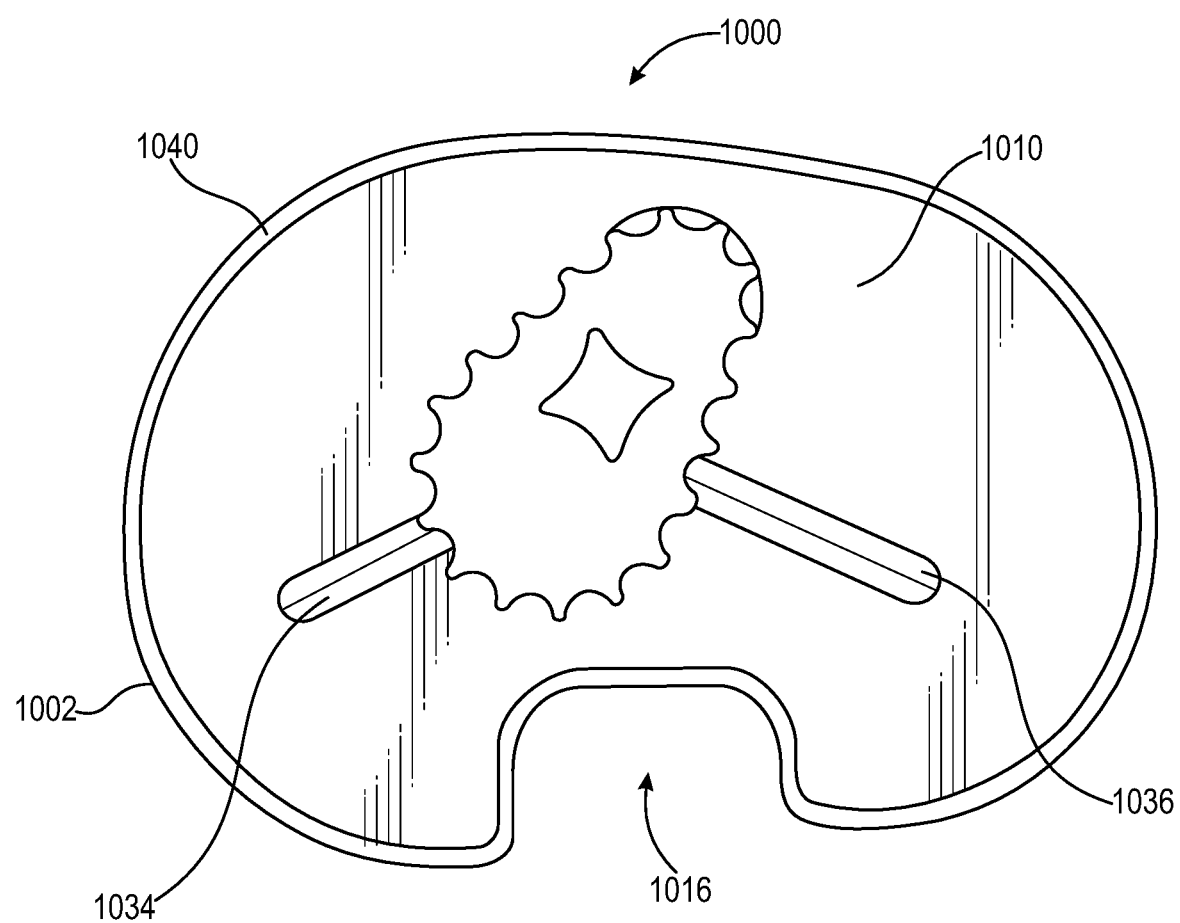
FIG. 28 is a top view of the tibial component illustrated in FIG. 27.
Figure 29:
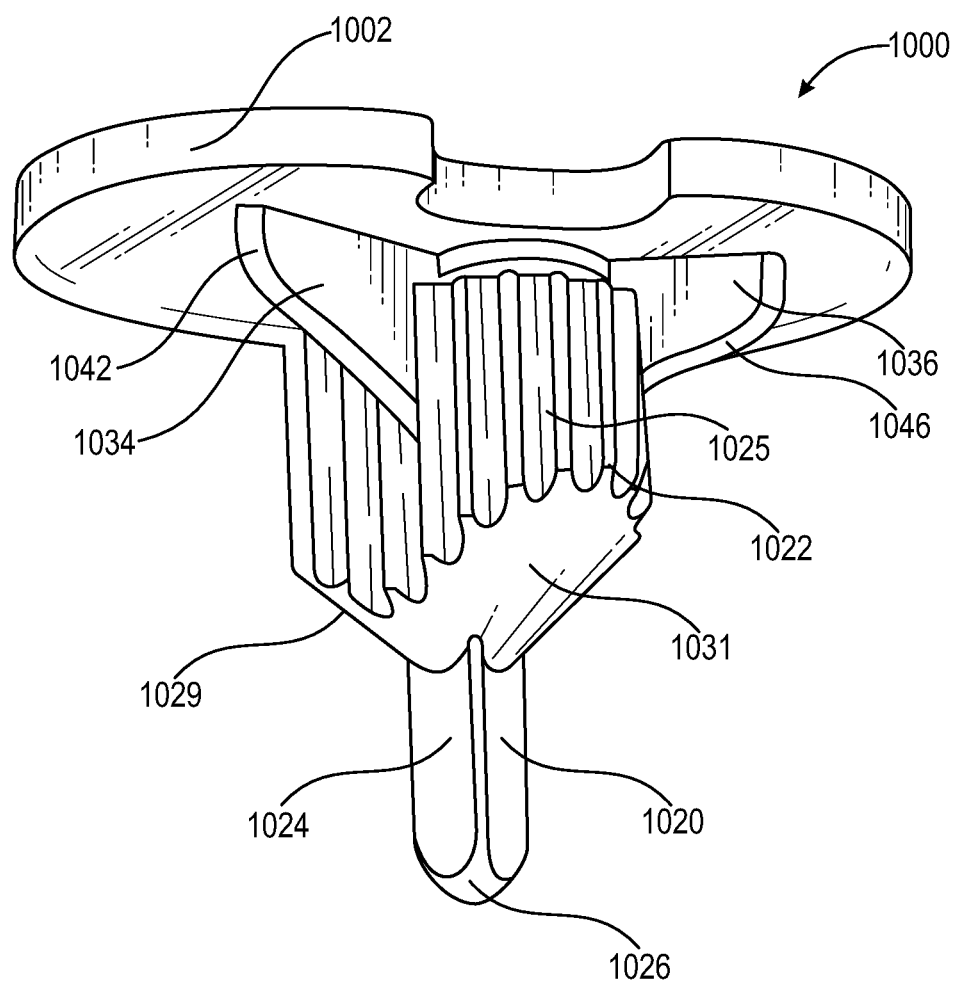
FIG. 29 is a perspective view of the tibial component illustrated in FIG. 27.
Figure 30:
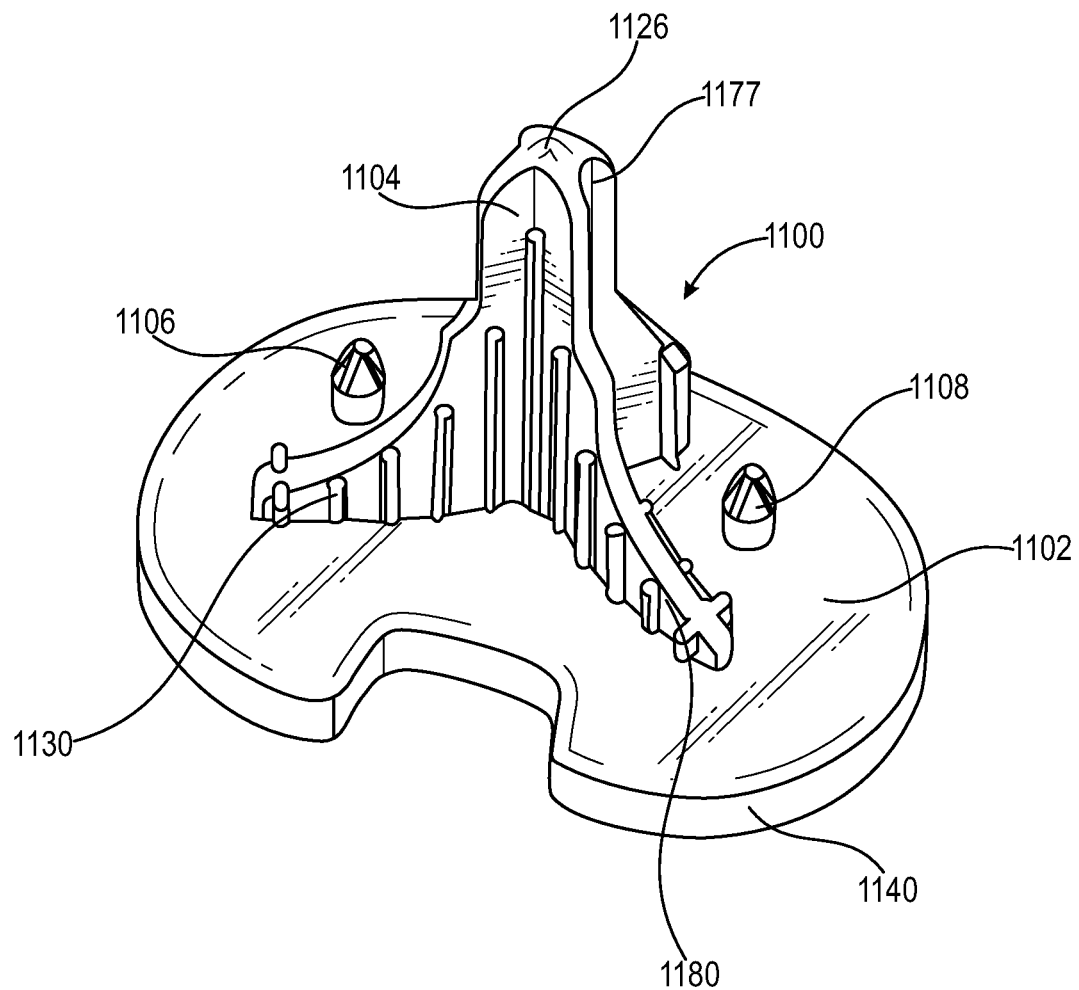
FIG. 30 is a perspective view of a tibial component according to a sixth embodiment.
Figure 31:
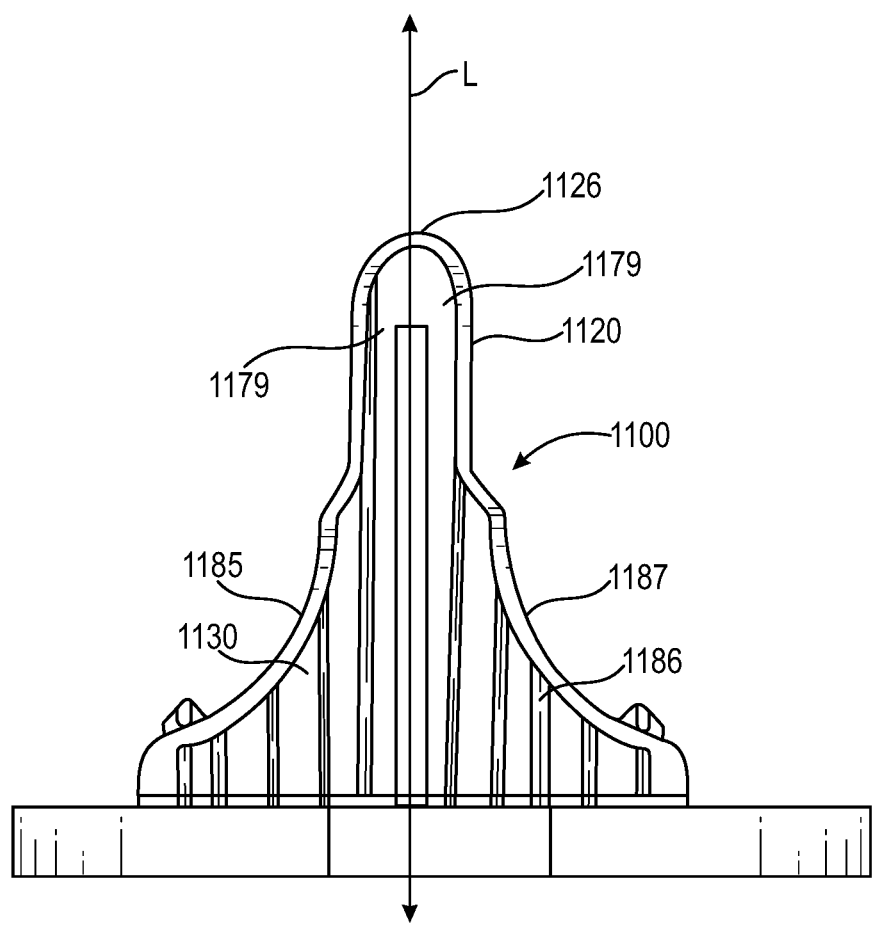
FIG. 31 is a rear view of the tibial component illustrated in FIG. 30.
Figure 32:
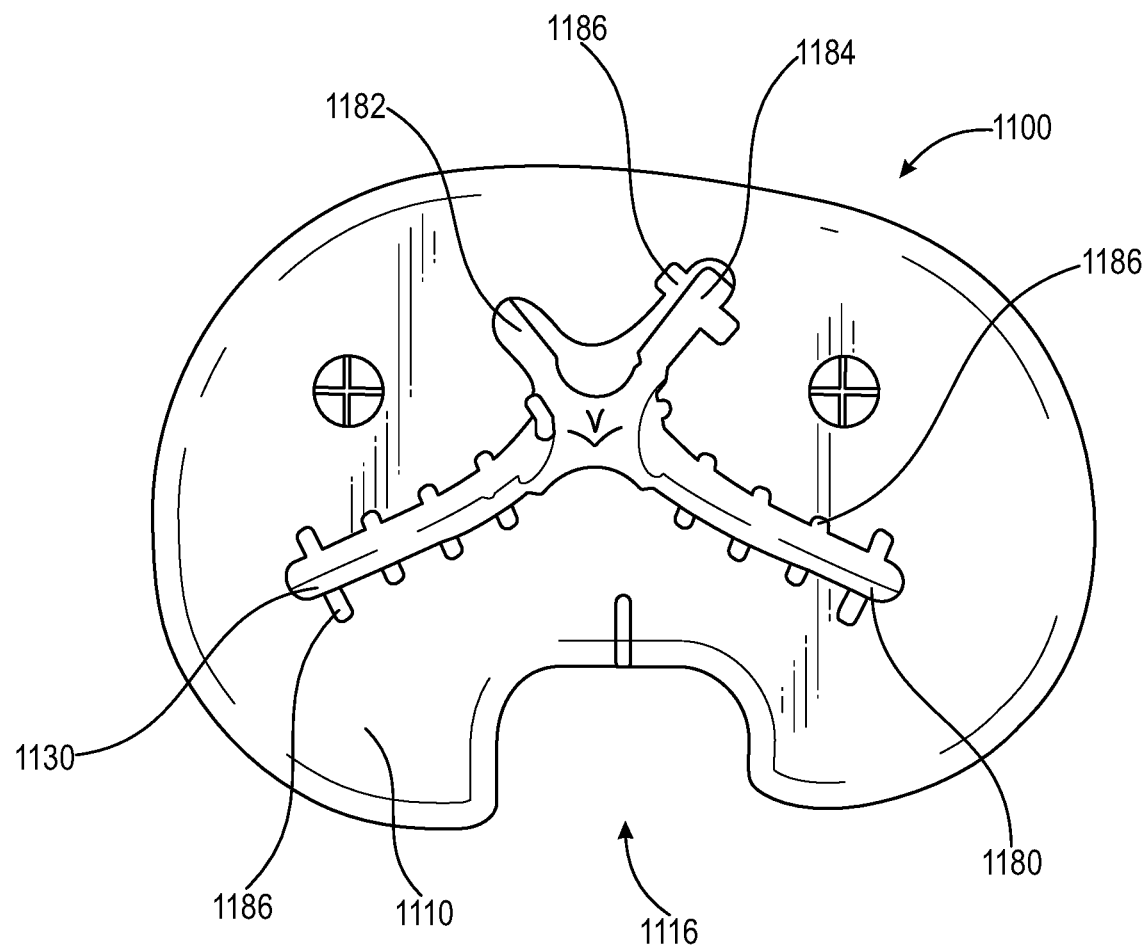
FIG. 32 is a top view of the tibial component illustrated in FIG. 30.
Figure 33:
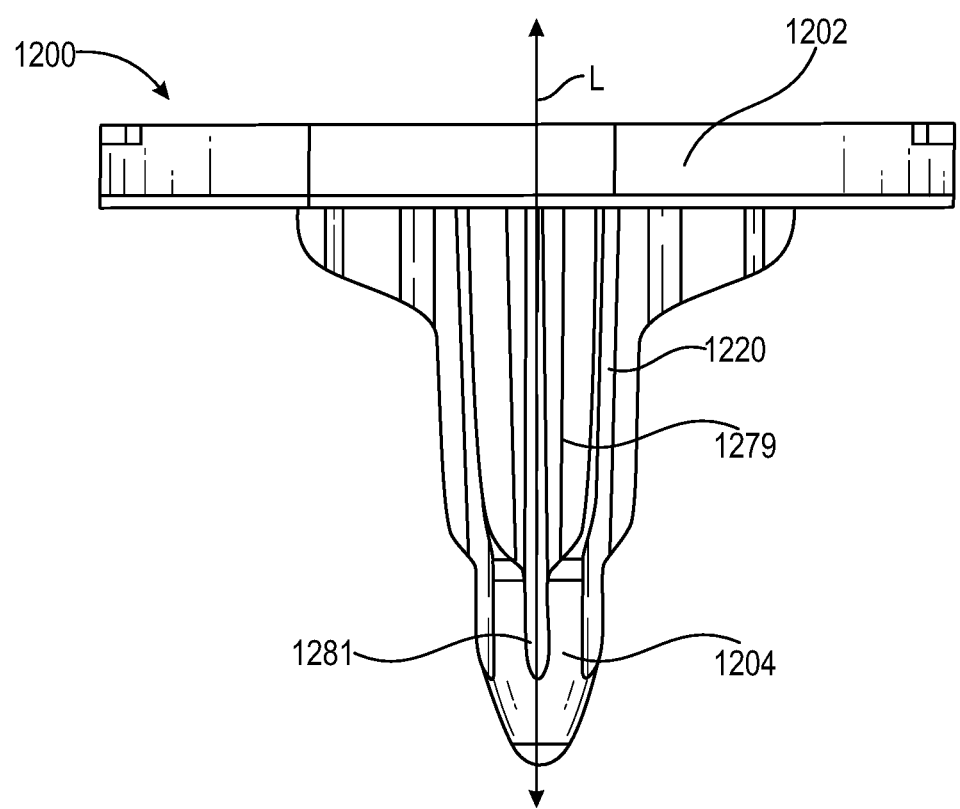
FIG. 33 is a rear view of a tibial component according to a seventh embodiment.
Figure 34:
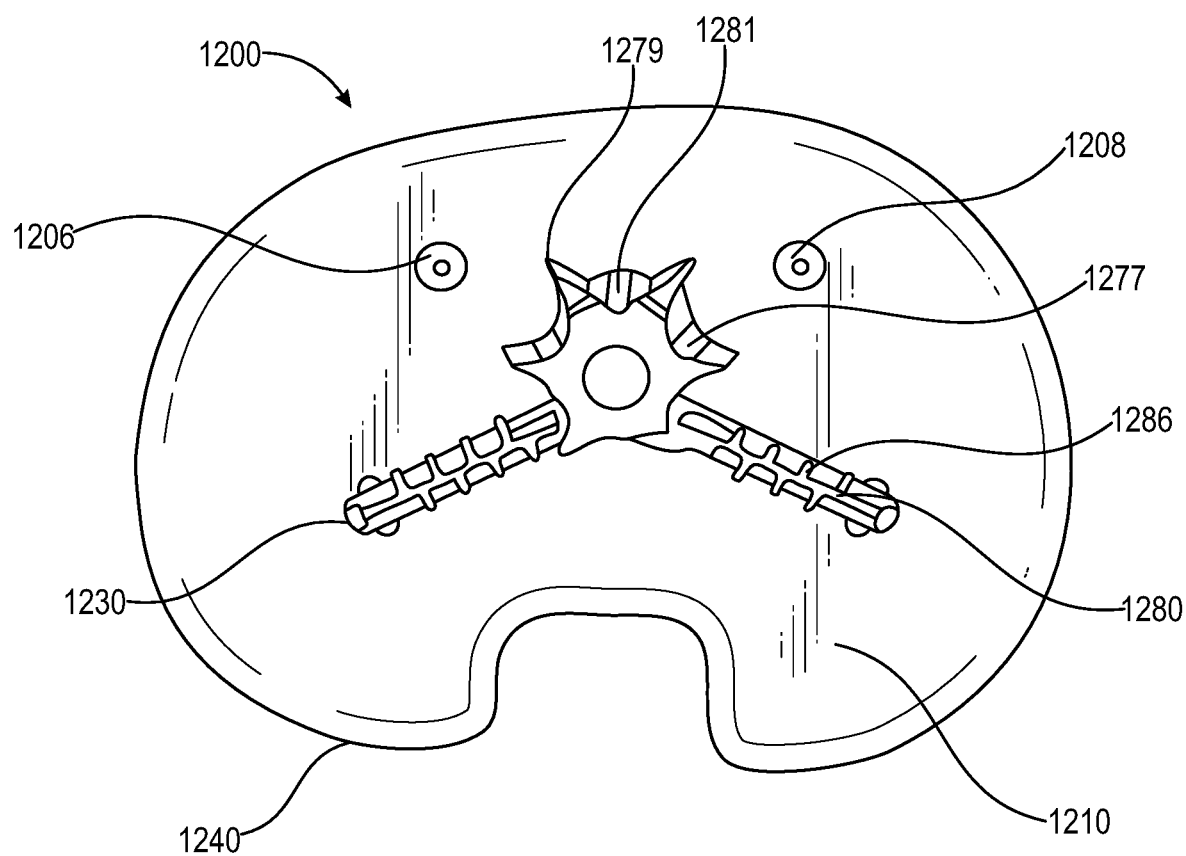
FIG. 34 is a top view of the tibial component illustrated in FIG. 33.
Figure 35:
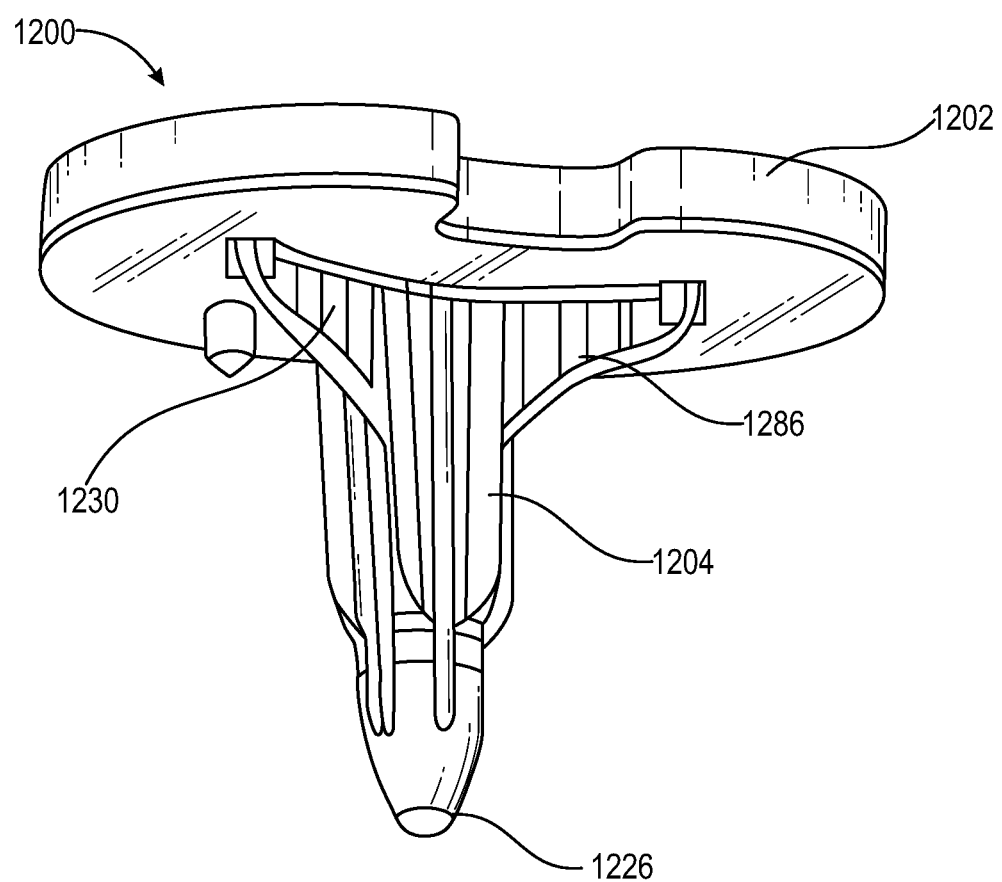
FIG. 35 is perspective view of the tibial component illustrated in FIG. 33.
Figure 36:
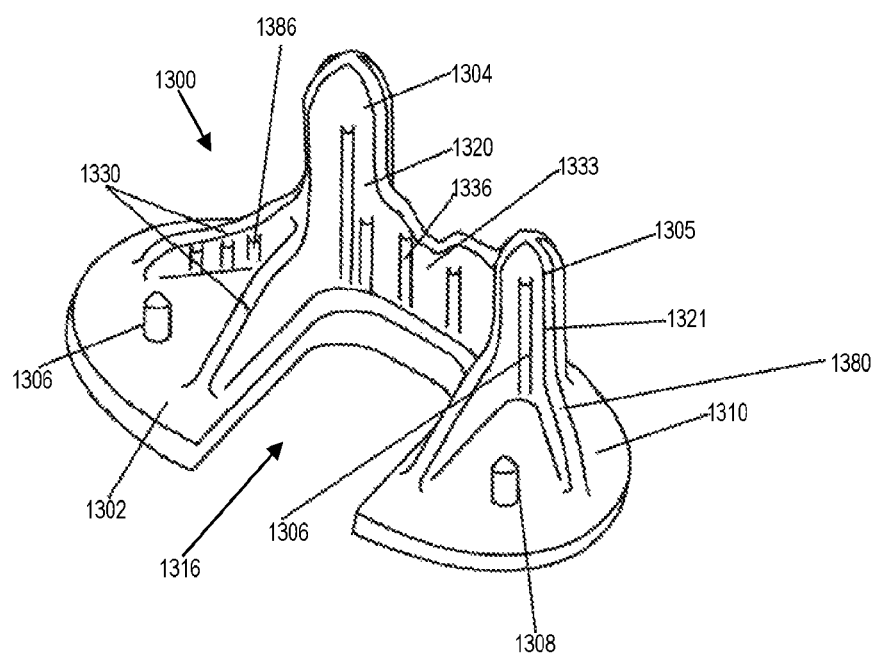
FIG. 36 is a perspective view of a tibial component according to a seventh embodiment.

With reference to FIGS. 1-4, illustrated therein is a non-limiting example of a tibial component 100, generally indicated with 100-series reference characters, according to one form. FIGS. 5-8 illustrate a tibial component 200, generally indicated with 200-series reference characters, according to one form. FIGS. 9-11 illustrate another tibial component, generally indicated with 300-series reference characters, implanted in bone with an anchor. Non-limiting examples of anchors are illustrated in FIGS. 12-20, however these and other forms of anchors can be used with any of the tibial components described herein. FIGS. 21-26 illustrate a tibial component 900, generally indicated with 900-series reference characters, according to one form, implanted in bone. FIGS. 27-29 illustrate a tibial component 1000, generally indicated with 1000-series reference characters, according to one form. FIGS. 30-32 illustrate a tibial component 1100, generally indicated with 1100-series reference characters, according to one form. FIGS. 33-35 illustrate a tibial component 1200, generally indicated with 1200-series reference characters, according to one form. FIG. 36 illustrates a tibial component 1300, generally indicated with 1300-series reference characters, according one form. A person of ordinary skill in the art would understand that one or more features from any of the disclosed embodiments may be combined. A person of ordinary skill in the art would understand that one size for each of the tibial components is illustrated and that any of the elements of the tibial components can vary in size as desired.

The tibial component 100 includes a tibial tray 102 connected to a support member 104. The support member 104 can be connected to the tibial tray 102 by any technique including but not limited to threaded, press-fit, adhesive, cement, or other techniques. In one form, the support member 104 is monolithic with the tibial tray 102. In the illustrated embodiment, the tibial component 100 also can include a first peg 106 and a second peg 108.

The tibial tray 102 includes an inferior side 110 opposite a superior side 112. The tibial tray 102 includes a lip or lock 114 on the superior side 112 for receiving and/or securing one or more articular inserts (not shown) to the tibial tray 102, such inserts designed to contact and articulate with a femoral orthopedic implant (not shown) in use. In the depicted embodiment, the lip or lock 114 is a shaped channel to receive and lock-in the articular insert. In other embodiments, the tibial tray 102 itself may include articular surfaces and does not require separate articular inserts. The tibial tray 102 shown in FIGS. 1 through 4 includes a posterior notch 116, which may be designed to allow preservation of the attachment site of a posterior cruciate ligament, although, in other embodiments, the tibial tray 102 may or may not include this or other notches or gaps for preserving one or both of the cruciate ligaments. In other words, the tibial tray, in some embodiments, may be for use in a cruciate sacrificing procedure, a posterior cruciate preserving procedure, or a bi-cruciate preserving procedure. One example embodiment of a tibial component useful in a bi-cruciate preserving procedure is illustrated in FIG. 36. In some embodiments, the tibial tray 102 may be used for a mobile bearing knee joint or a fixed bearing knee joint. It will be appreciated that a variety of upper surface and peripheral shapes are possible according to various embodiments and that such shapes can be influenced, at least in part, by strength requirements for the tray. For example, in some embodiments, a cruciate notch or dovetail mechanism may be used, but also may act as a stress-riser.

The support member 104 is positioned on the inferior side 110 of the tibial tray 102. The support member 104 has a stem portion 120 that extends away from the inferior side 110 along a longitudinal axis L. In the illustrated embodiment, the longitudinal axis L is substantially perpendicular to the inferior side 110 of the tibial tray 102 in the medial-lateral direction, but other angles may be used. Additionally, some embodiments include the tibial tray 102 having a slope in the anterior-posterior direction. For example, the tibial tray 102 can have a 3-7 degree posterior slope. Alternatively, the tibial tray 102 can have a zero degree slope. The stem portion 120 is positioned offset from a center of the tibial tray 102. The stem portion 120 is medialized slightly from the center of the tibial tray 102. For example, the stem portion 120 can be medialized 1-3 mm from the center of the tibial tray 102. In other forms, the stem portion 120 may be centered on the tibial tray 102. The stem portion 104 includes a first portion 122 adjacent the inferior side 110 of the tibial tray 102 and a second portion 124 that extends away from the first portion 122. The first portion 122 has a first cross sectional area and the second portion 124 has a second cross sectional area wherein the first cross sectional area is larger than the second cross sectional area in the illustrated embodiment. In other configurations, the second portion 124 can have the same cross sectional area and shape as the first portion 122. In the illustrated embodiment, the first portion 122 is cylindrical and the second portion 124 tapers from the first portion 122 to a tip 126. The stem portion 104 has a length that is sized to promote varus-valgus stability and resistance of the tibial tray 104 to liftoff from bone.

In the illustrated embodiment, the support member 104 includes several fins 130 that are equally spaced from each other. There are four fins 130 wherein each of the fins 130 is rotated about 90 degrees from an adjacent one of the fins 130 wherein each of the fins 130 extend in opposite directions. In other embodiments, the support member 104 can include a greater or lesser number of fins 130. Moreover, in other forms, the fins 130 can be spaced equally from each other or in another arrangement as desired. The fins 130 extend along the support member 104 towards the second portion 124 in a tapering configuration. The fins 130 assist in rotational stability and help with implantation and alignment of the tibial tray 102 in bone upon implantation. Any or all of the fins 130 can also be sized to a maximum that is implantable based on the anatomy of the patient.

The support member 104 includes a first arm 134 angled relative to a second arm 136 mounted on the inferior side 110 of the tibial tray 102. The first arm 134 and the second arm 136 can be attached to or monolithic with the support member 104. In FIGS. 1-4, the first arm 134 is angled relative to the second arm 136, but in other embodiments the first and second arms 134 and 136 are substantially aligned with one another. An angle A between the first arm 134 and the second arm 136 can range from about 10 degrees to about 180 degrees. In the illustrated embodiment, the angle A ranges between 120 degrees to about 130 degrees. In the illustrated embodiment, the first arm 134 and the second arm 136 each have a triangular shape and are substantially flat. In other configurations, the first arm 134 and the second arm 136 can be shaped differently and/or shaped differently from each other. In one form, the first arm 134 and the second arm 136 curve or curl towards the posterior notch 116. The first arm 134 and the second arm 136 extend along the support member 104 towards the second portion 124; however, the first and second arms 134 and 136 are shorter or smaller than the fins 130 and do not extend as far as the fins 130 along the support member 104. Each of the first and second arms 134 and 136 has a length that extends towards a rim or periphery edge 140 of the tibial tray 102. The first and second arms 134 and 136 each have a sharp edge 142 and 144, respectively. The first and second arms 134 and 136 assist with rotational stability of the tibial tray 102 in bone upon implantation.

Beneficially, the fins 130, first arm 134, and second arm 136 provide more rotational resistance and strength for the tibial component 100 when it is implanted. The unique configuration of fins 130, first arm 134, second arm 136, and support member 104 improve fixation between the tibial tray 102 and bone post-operatively. Moreover, fins 130 positioned on the anterior side of the tibial tray 102 are more sensitive to anatomic dimension than the fins 130 positioned on the posterior side therefore the size, location, and position of the anterior fins 130 on the tibial tray 102 are more sensitive than the posterior fins 130. The features of the tibial components described herein correspond to different features of the bone at a variety of cross sectional shapes. Similarly, the unique arrangement and configuration of these components in tibial components provide similar benefits and other benefits as described below.

As mentioned previously, in the illustrated embodiment, the tibial component 100 also can include a first peg 106 and a second peg 108 mounted on the inferior side 110. The first peg 106 and the second peg 108 are positioned near the rim or periphery edge 140. The first peg 106 and the second peg 108 approach the tibial plateau for added stability of the tibial tray 102, and enter into denser bone than in the central canal upon implantation. Additional pegs can be mounted on the inferior side 110 as desired.

Turning now to FIGS. 5-8, a tibial component 200 is illustrated and includes certain features which correspond to those described above in connection with the tibial component 100 illustrated in FIGS. 1-4. Unless indicated otherwise, similar reference characters are used to indicate similar elements and features. For example, the tibial component 200 includes a tibial tray 202, a support member 204, a first arm 234, a second arm 236, a first peg 206, and a second peg 208 which respectively correspond to the tibial tray 102, the support member 104, the first arm 134, the second arm 136, the first peg 106, and the second peg 108 as described above. In the interest of conciseness, the following description focuses primarily on features of the tibial component 200 which may not necessarily have been described above with reference to the tibial component 100.

The support member 204 is positioned on the inferior side 210 of the tibial tray 202. The support member 204 has a stem portion 220 that extends away from the inferior side 210 along a longitudinal axis L that is substantially perpendicular to the inferior side 210 of the tibial tray 202. In other forms, the longitudinal axis L of the stem portion 220 may not be perpendicular to the interior side 210 of the tibial tray 202. Additionally, some embodiments include the tibial tray 202 having a slope in the anterior-posterior direction. For example, the tibial tray 202 can have a 3-7 degree posterior slope. Alternatively, the tibial tray 202 can have a zero degree slope. The stem portion 204 has an elongated cross sectional shape with a pair of semi-circular or convex portions 250 and 252 that are separated by a pair of concave portions 254 and 256. In other configurations, the stem portion 220 can have the same cross sectional area and shape as the stem portion 120. In the illustrated embodiment, the stem portion 220 tapers slightly at a tip 226. The stem portion 120 is positioned offset from a center of the tibial tray 202. The stem portion 220 is medialized slightly from the center of the tibial tray 202. For example, the stem portion 220 can be medialized 1-3 mm from the center of the tibial tray 202. In other forms, the stem portion 220 may be centered on the tibial tray 202.

In the illustrated embodiment, the support member 204 includes a first fin 230 and a second fin 232 wherein each have a curvature or radius that arches towards the support member 204. The first fin 230 has a thicker portion 238 that extends to a thinner tip portion 260. Similarly, the second fin 232 has a thicker portion 238 that extends to a thinner tip portion 262. The first fin 230 is rotated about 180 degrees from the second fin 232 wherein the first fin 230 extends in an opposite direction from the second fin 232. In other embodiments, the support member 204 can include a greater or lesser number of fins 230 and/or 232. Moreover, in other forms, the first fin 230 and the second fin 232 can be spaced in another arrangement as desired. The first fin 230 and the second fin 232 extend along the support member 204 towards the tip 226, wherein the first fin 230 has an end portion 238 adjacent a tapered end portion 239 and the second fin 232 has an end portion 241 adjacent a tapered end portion 243. The first fin 230 and the second fin 232 assist in rotational stability and help with implantation and alignment of the tibial tray 202 in bone when implanted.

The first arm 234 and the second arm 236 can be straight as illustrated or have a curvature or radius that arches towards the support member 204 or curl away from the rim 240.

As discussed above, first fin 230 and second fin 232 each have a curvature or radius R that arches towards the support member which can be beneficial during implantation if the bone is very hard. The first fin 230 and the second fin 232 can have also have an angle. If either an angle or radii are present in the first fin 230 and/or the second fin 232 then the angle or radii are typically large. More specifically, if the curvature is present, then it can be in the 2-4" radii range, down to sharper curves such as ½" or less radii. If instead of curved fins, straight fins are used in very hard bone, then it is possible that the straight fins can act as wedges, which may fracture bone. However, because the first and second fins 230 and 232 curve away from or point away from the rim or perimeter 240 then if a fracture did occur in bone, the fracture would radiate inward as compared to outward, and therefore a tibia fracture would most likely not occur.

Another embodiment of the tibial component can include the addition of a fixation screw or anchor to the distal side of the tibial component. Traditional screw fixation on tibial trays is from the superior to inferior direction and through the tibial tray itself, thus anchoring the tibial tray down to the plateau. As disclosed herein, screws or anchors can enter in an anterior to posterior direction, and lock on to the tibial component within the fin itself or other distally placed feature, thus anchoring the tibial component to the proximal tibia. The screws or anchors can be permanent or temporary, and may be resorbable. Examples of anchors or screws are illustrated in FIGS. 12-20. The anchors can be an optional feature, a decision to be made intraoperatively if it was found that the bone quality was not sufficient to support a cementless application of the tibial component, or if a user was not pleased with the degree of initial fixation that he/she was experiencing in a porous case.

Turning now to FIGS. 9-11, a tibial component 300 is illustrated and includes certain features which correspond to those described above in connection with the tibial component 100 illustrated in FIGS. 1-4. Unless indicated otherwise, similar reference characters are used to indicate similar elements and features. For example, the tibial component 300 includes a tibial tray 302, a support member 304, a first arm 334, and a second arm 336, which respectively correspond to the tibial tray 102, the support member 104, the first arm 134, and the second arm 136 as described above. In the interest of conciseness, the following description focuses primarily on features of the tibial component 300 which may not necessarily have been described above with reference to the tibial component 100.

The support member 304 is positioned on the inferior side 310 of the tibial tray 302. The support member 304 has a stem portion 320 that extends away from the inferior side 310 along a longitudinal axis L that is substantially perpendicular to the inferior side 310 of the tibial tray 302. In other forms, the longitudinal axis L of the stem portion 320 may not be perpendicular to the inferior side 310 of the tibial tray 302. The stem portion 320 is a cylindrical shape. In other configurations, the stem portion 320 can have the same cross sectional area and shape as the stem portion 120 or the stem portion 220.

In the illustrated embodiment, the support member 304 includes a first fin 330 and a second fin 332. In one form, the first arm 334 and the second arm 336 are configured similarly as the first fin 330 and the second fin 332, respectively. The first fin 330 and the second fin 332 each have a triangular shape and are substantially flat. The first fin 330 is rotated about 180 degrees from the second fin 332 wherein the first fin 330 extends in an opposite direction from the second fin 332. In other embodiments, the support member 304 can include a greater or lesser number of fins 330 and/or 332. Moreover, in other forms, the first fin 330 and the second fin 332 can be spaced in another arrangement as desired. The first fin 330 and the second fin 332 extend along the support member 304 towards the tip 326. The first fin 330 includes a first hole 366 and the second fin 332 includes a second hole 368. In other embodiments, the first fin 330 and the second fin 332 include additional holes or may not include any holes. The first hole 366 and the second hole 368 are each sized to receive an anchor 400 or other type of fixation device or screw that is positioned through a distal side 370 towards a posterior side 372 of the tibial component 300.

Additional embodiments of anchors 500, 600, 700, and 800 are illustrated in FIGS. 12-20 wherein any of these anchors or other anchors not illustrated may be used with any of the tibial components described herein. A variety of bone anchors or screw designs would be applicable with any of the tibial components, and several of those embodiments are included below here. These embodiments can include cylindrical or tapered designs, hollow or solid cores, longitudinal rails or fins, smooth fins or interrupted or staggered fins, as well as lateral rings or ribs, and other configurations. Additionally, the anchors 500, 600, 700, and 800 are implanted through any of the fins or arms however it is preferred that the anchors 500, 600, 700, and 800 are not implanted through the tibial trays.

Figure 12:
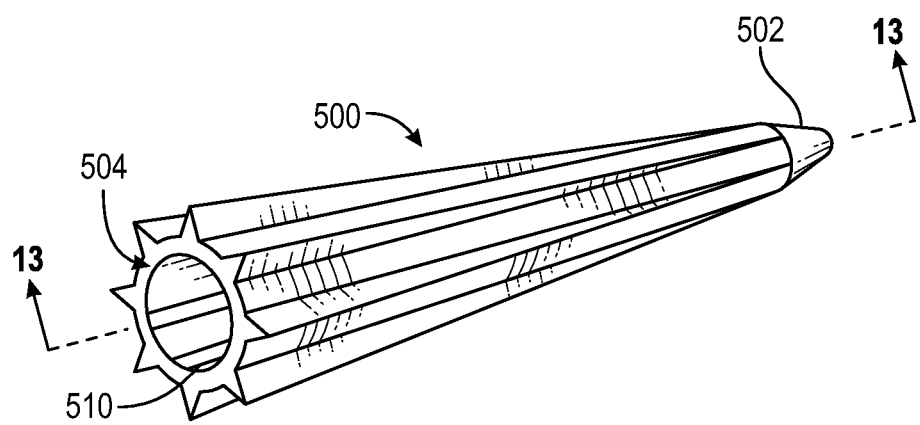
FIG. 12 is a first perspective view of an anchor according to one embodiment.
Figure 13:
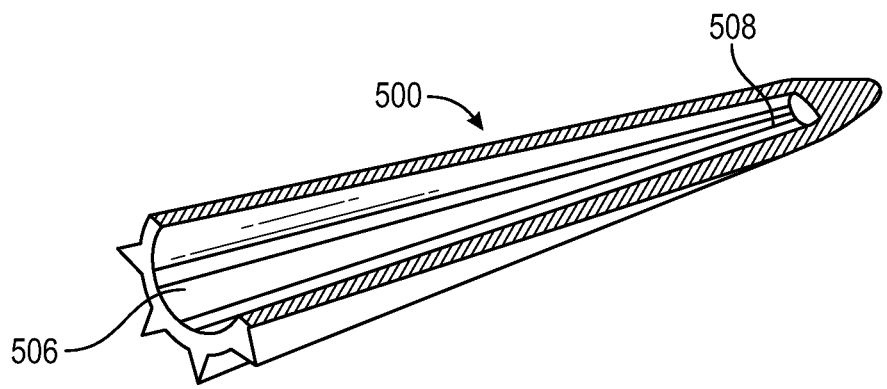
FIG. 13 is a sectional perspective view of the anchor illustrated in FIG. 12.
Figure 14:
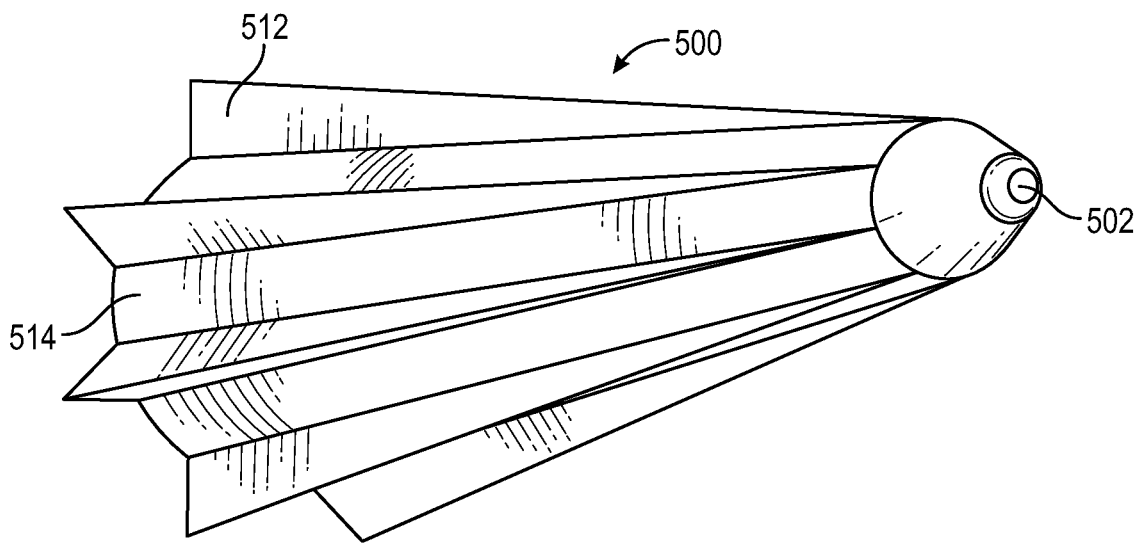
FIG. 14 is a second perspective view of the anchor illustrated in FIG. 12.

Turning now to FIGS. 12-14, an anchor 500 is illustrated. Anchor 500 is a conical shape having a length defined by an insertion tip portion 502 that is opposite an installation end portion 504. The anchor 500 includes an orifice or cavity 506 that tapers from an opening 510 at the installation end portion 504 to an end portion 508 at the insertion tip portion 502. The anchor 500 includes a plurality of longitudinal rails or fins 512 that span from the insertion tip portion 502 to the installation end portion 504 along an outer surface 514.

Figure 15:
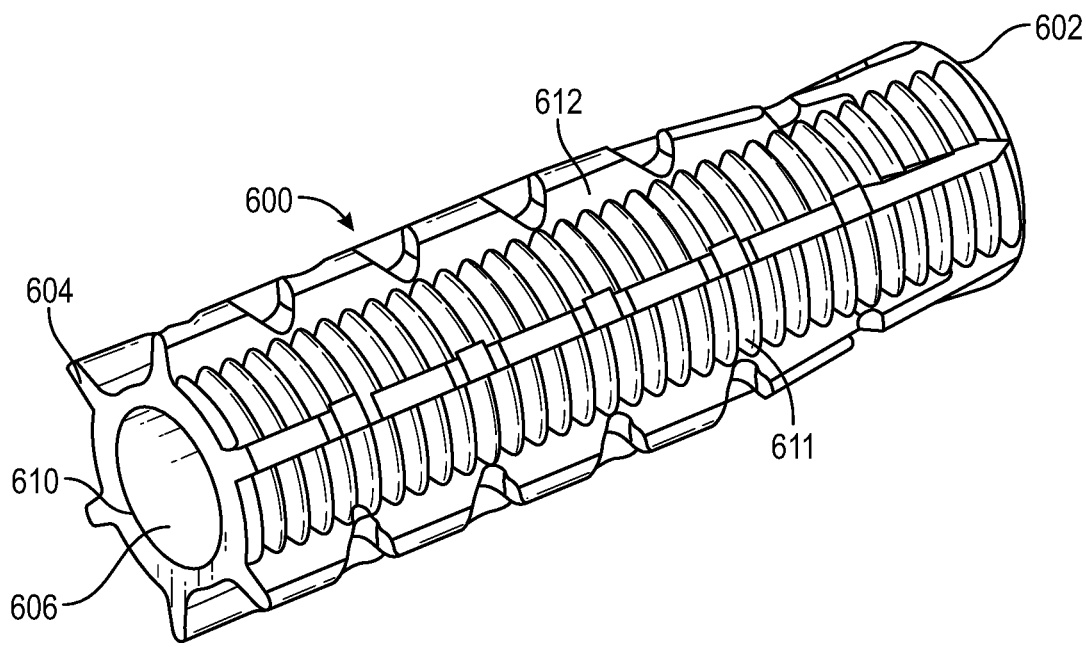
FIG. 15 is a first perspective view of an anchor according to second embodiment.
Figure 16:
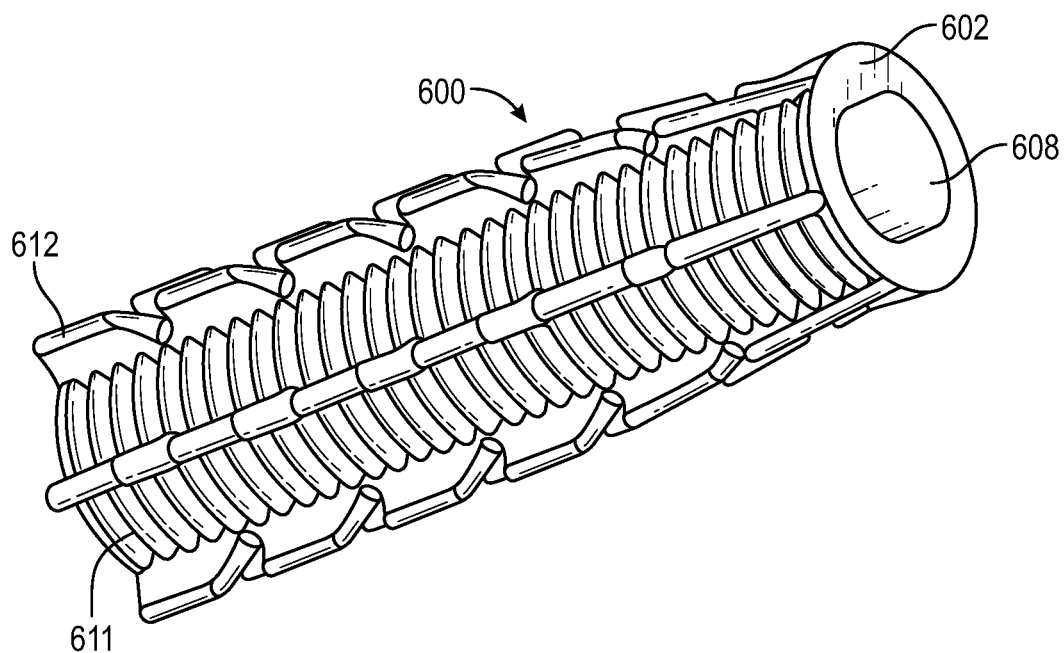
FIG. 16 is a second perspective view of the anchor illustrated in FIG. 15.

Turning now to FIGS. 15 and 16, an anchor 600 is illustrated. Anchor 600 is a tubular shape having a length defined by an insertion end portion 602 that is opposite an installation end portion 604. The anchor 600 includes a cylindrical passageway 606 that spans from a first opening 610 at the installation end portion 604 to a second opening 608 at the insertion end portion 602. The anchor 600 includes a plurality of lateral ribs 611 that span around the outer surface of the anchor 600 and a plurality of longitudinal barbs 612 that span along the length of the anchor 600. The longitudinal barbs 612 are arranged in an alternating relationship with the lateral ribs 611. In one form, the lateral ribs 611 have a shorter length than the longitudinal barbs 612. The longitudinal barbs 612 create the initial bit and rotational resistance of the anchor 600. The lateral ribs 611 increase the pull out resistance of the anchor 600. As examples, anchor 600 could be a HEALICOIL® suture anchor or a REGENESORB® suture anchor. HEALICOIL® and REGENESORB® are registered trademarks of Smith & Nephew, Inc. located in Memphis, Tennessee.

Figure 17:
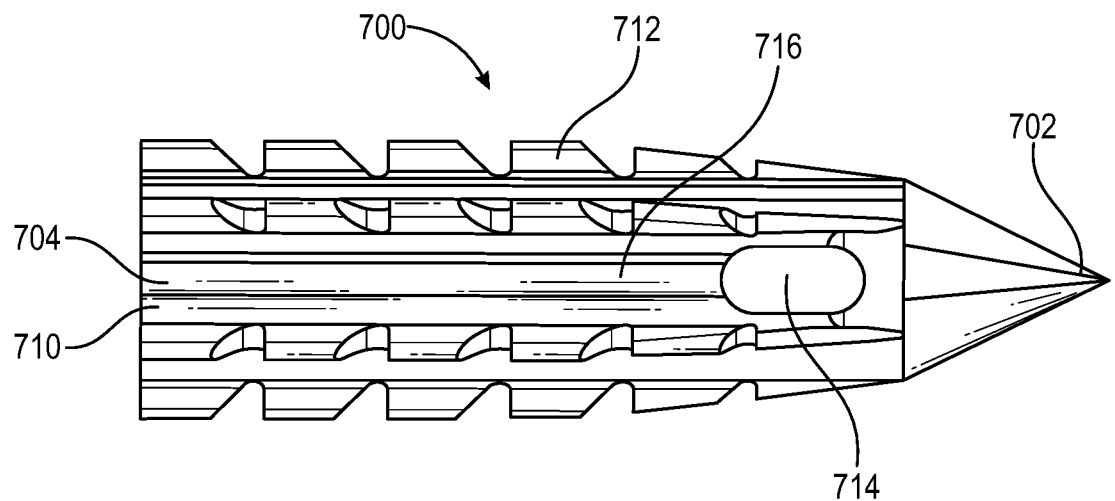
FIG. 17 is a front view of an anchor according to a third embodiment.

Turning now to FIG. 17, an anchor 700 is illustrated. Anchor 700 is a tubular shape having a length defined by an insertion end portion 702 that is opposite an installation end portion 704. The insertion end portion 702 is a solid cone shape. The anchor 700 includes a cylindrical cavity 706 that extends from an opening 710 at the installation end portion 704 to an end portion (not illustrated) near the insertion end portion 702. The anchor 700 includes a plurality of longitudinal barbs 712 that span along the length of the anchor 700. The anchor 700 also includes a hole 714 that extends through a wall 716 of the anchor 700. The hole 714 is sized to receive medical devices or other medical instruments as needed.

Figure 18:
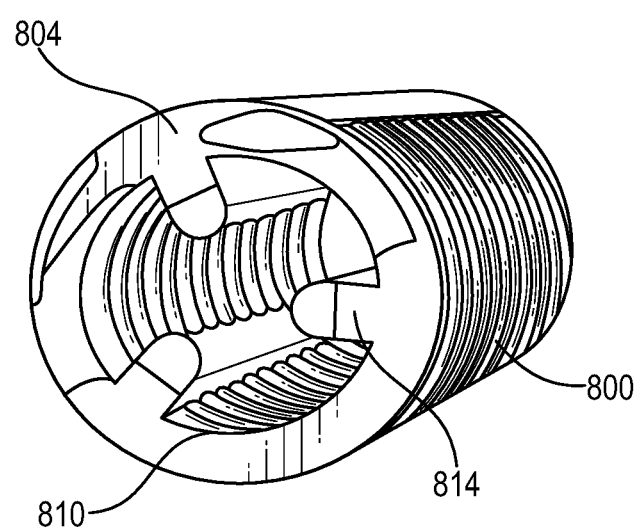
FIG. 18 is a first perspective view of an anchor according to a fourth embodiment.
Figure 19:
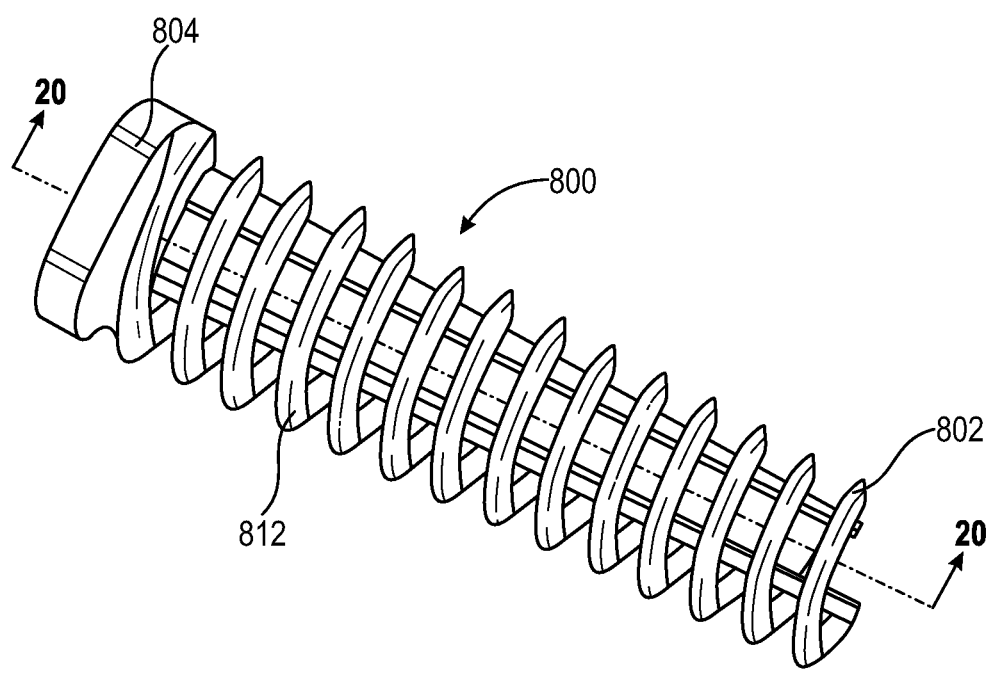
FIG. 19 is a front view of the anchor illustrated in FIG. 18.
Figure 20:
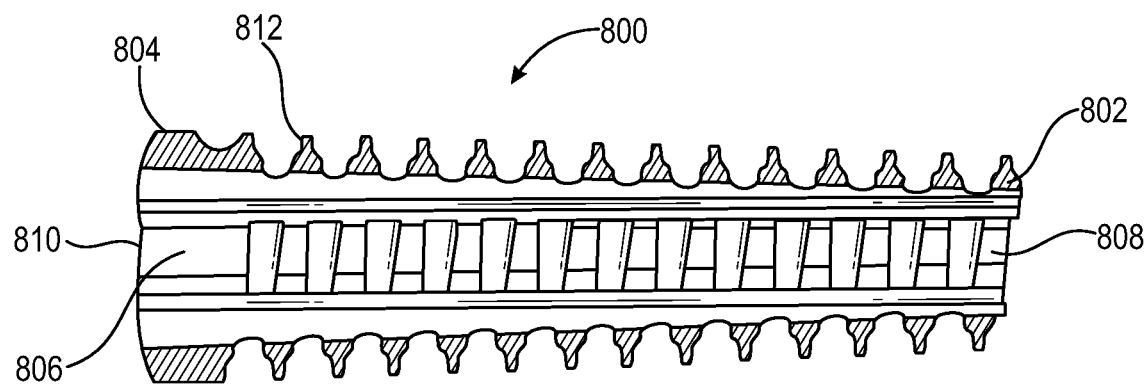
FIG. 20 is a sectional view of the anchor illustrated in FIG. 19.
Figure 22:
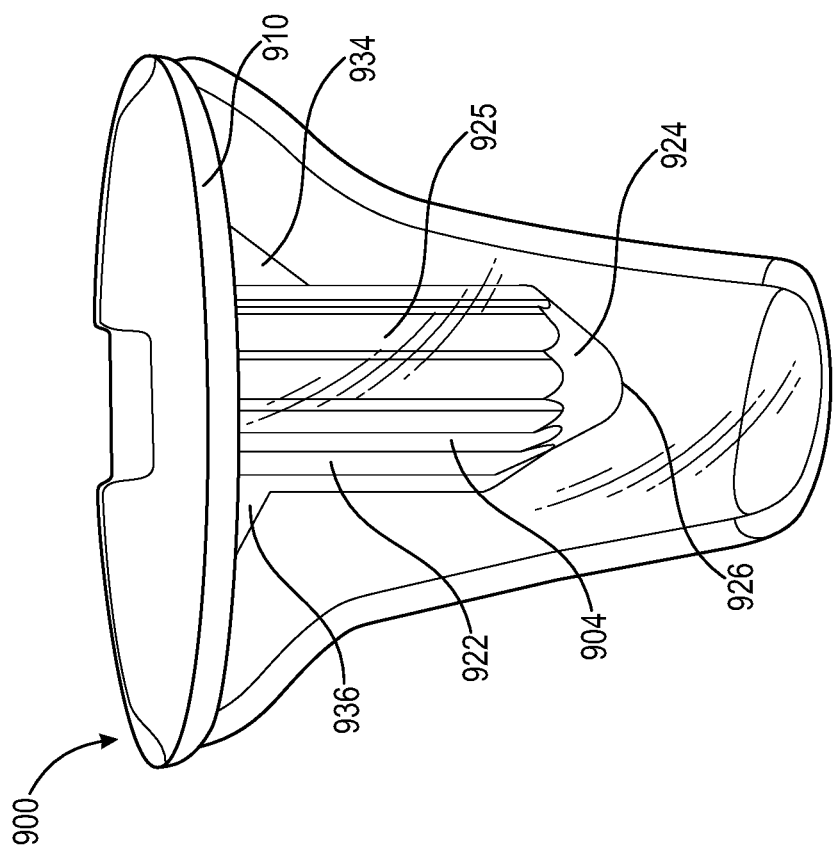
FIG. 22 is a front view of the tibial component illustrated in FIG. 21.
Figure 21:
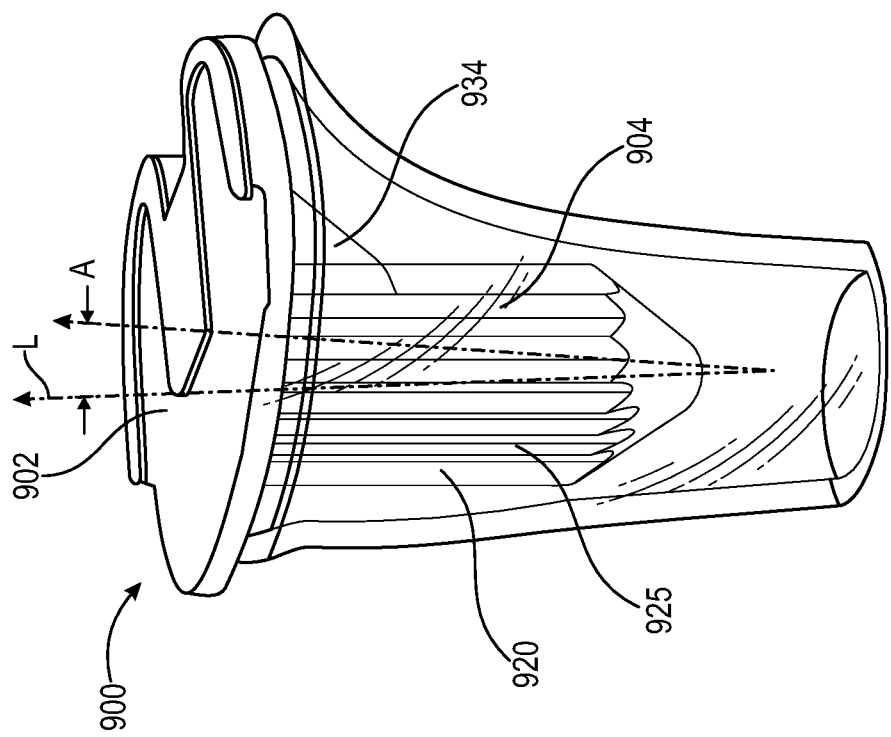
FIG. 21 is a first side view of a tibial component according to a fourth embodiment.
Figure 24:
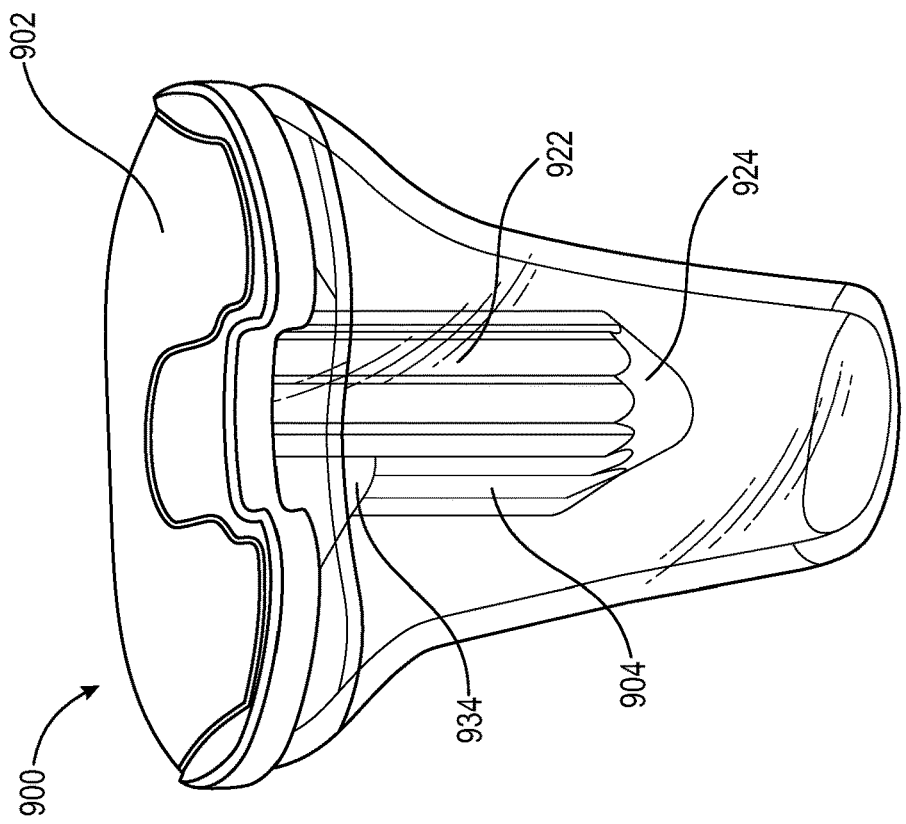
FIG. 24 is a rear view of the tibial component illustrated in FIG. 21.
Figure 23:
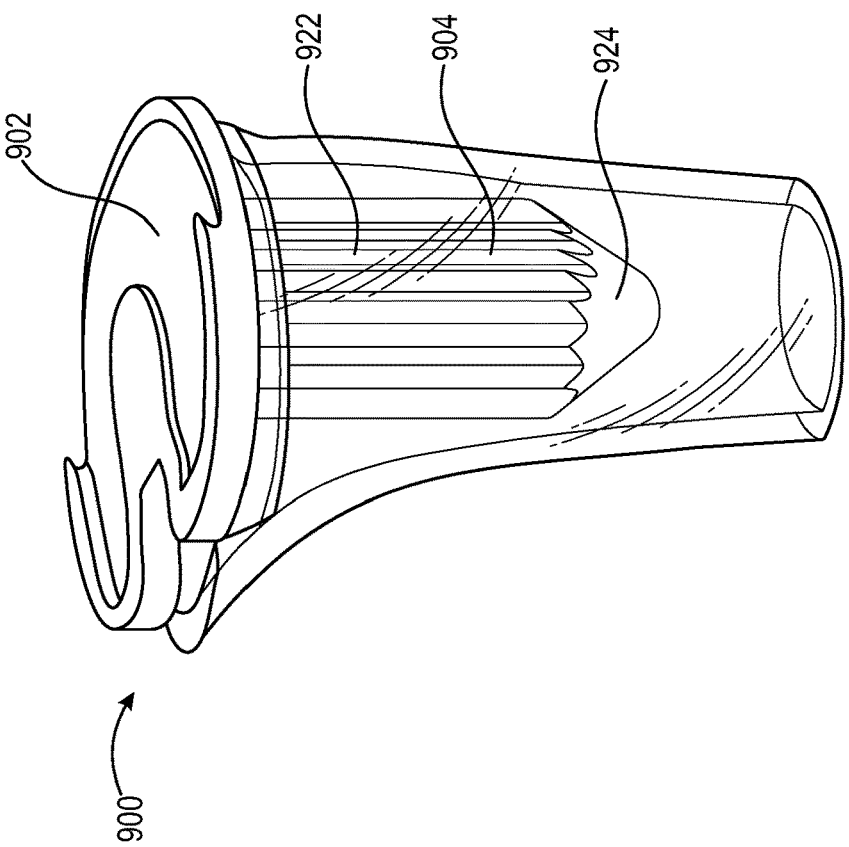
FIG. 23 is a second side view of the tibial component illustrated in FIG. 21.
Figure 25:
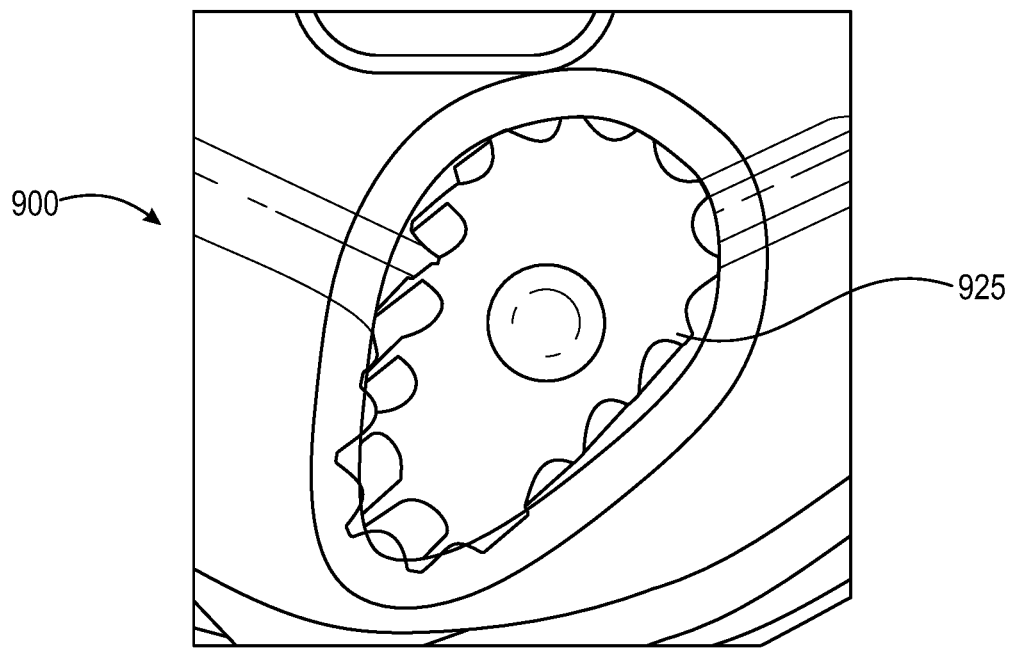
FIG. 25 is a partial end view of the tibial component illustrated in FIG. 21 implanted in bone.
Figure 26:
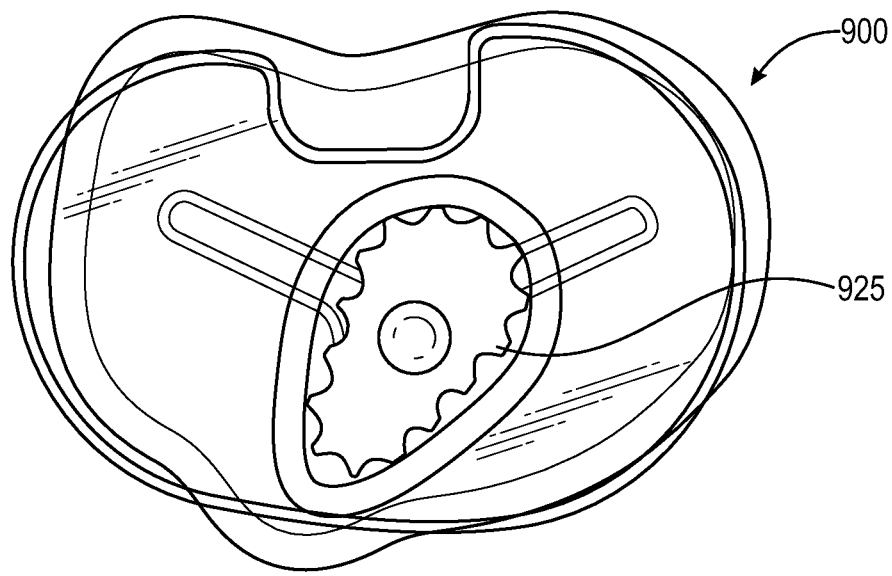
FIG. 26 is an end view of the tibial component illustrated in FIG. 25.

Turning now to FIGS. 18-20, an anchor 800 is illustrated. Anchor 800 is a tubular shape having a length defined by an insertion end portion 802 that is opposite an installation end portion 804. The anchor 800 includes a cylindrical passageway 806 that extends from a first opening 810 at the installation end portion 804 to a second opening 808 at the insertion end portion 802. The anchor 800 includes a spiral or helical wire 812 that spans circumferentially along the length of the anchor 800. The installation end portion 804 includes a plurality of tabs 814 sized to receive medical devices or other medical instruments as needed. As examples, anchor 800 could be a HEALICOIL® suture anchor or a REGENESORB® suture anchor. HEALICOIL® and REGENESORBR are registered trademarks of Smith & Nephew, Inc. located in Memphis, Tennessee.

The anchors described herein can be made of a bioabsorbable and/or biocompatible material, such as a monomer or a hard polymer (bioplastic) that will resorb by hydrolysis (for example) within the body over 6-24 months, based on clinical need. Polymer options for the anchors include, but are not limited to PLA, PLGA, PLGLA, PLDA or similar materials Metal can be used for the anchors as well. In order to improve the fixation and/or holding strength of the screw or anchor, it may be preferable to choose a polymer formulation that is designed to swell with liquid absorption. This swelling would increase the interference forces inside the screw or anchor to bone interface and improve the overall holding strength of the tibial component. The swelling also would allow for a line-to-line fit, or over-preparation situation, allowing for an easier or less aggressive surgical technique, and when the anchor or screw absorbs blood or other fluids at the surgical site, the fixation strength would increase to a desired level.

In some conditions upon implantation of the tibial component, in order to also buffer or neutralize the immediate microenvironment around the hydrolysis site (immediately around the tibial component), it may be desirable to add a basic component to neutralize the acidic byproduct of the polymers. Also, a composite of additional bone-friendly agents such as hydroxyapatite, calcium apatite tricalcium phosphate, or similar may be desirable for the anchor as well. The choice of bulk erosion or surface erosion could be controlled as well, based on the polymer(s) option chosen for the material of the anchor. Finally, the polymer component also could act as a carrier for any number or metabolic agents. These would include short-term agents such as growth factors including demineralized bone matrix (DBM) or bone morphogenic proteins (BMPs) or other molecules (parathyroid hormone (PTH) for example) to amplify, signal, recruit, and/or encourage bone ingrowth.

Special consideration is recommended in patients with osteoporosis, which is the most common metabolic bone disease in the United States. Healing process is prolonged in fragile osteoporotic bone, characterized by loss of bone mass and deteriorating bone structure. For this group of patients, the polymer for the anchor also could act as a carrier for long-term drug delivery, in order to supplement the healing process or augment the patients' normal metabolic system. This pathway can be successfully used to counteract complications due to metabolic diseases, osteoporotic therapy (bisphosphonates, alendronates), chemotherapy for oncology patients, etc. The polymer component also could act as a carrier for autologous platelet rich plasma (PRP) treatment. PRP therapy has been successfully used in orthopedics to relieve pain and promote healing of various musculoskeletal conditions, due to the growth factors that are released from platelets.

Local antibacterial carriers or coatings can be used for infection control and/or prevention (silver, zinc, antibiotics, for example), as well as pain control/relief via NSAID or similar. These carriers or coatings can be applied as layer onto the anchor. With localized, time-release delivery, the therapeutic dosage would likely be much smaller than a similar systemic dosage, thus reducing risk of contraindications with other drug combinations, or toxicity concerns with high dosages of pharmaceutical agents. Localized pain medication also may be a preferred option, especially because cementless tibial trays implanted in patients can experience greater levels of pain compared to their cemented counterparts. The release profile could be tailored such that a larger bolus of pain medication is released immediately post-op and phased down after the first 2-4 weeks.

Turning now to FIGS. 21-26, a tibial component 900 is illustrated and includes certain features which correspond to those described above in connection with the tibial component 100 illustrated in FIGS. 1-4. Unless indicated otherwise, similar reference characters are used to indicate similar elements and features. For example, the tibial component 900 includes a tibial tray 902, a support member 904, a first arm 934, and a second arm 936, which respectively correspond to the tibial tray 102, the support member 104, the first arm 134, and the second arm 136 as described above. In the interest of conciseness, the following description focuses primarily on features of the tibial component 900 which may not necessarily have been described above with reference to the tibial component 100.

In one form, the tibial tray 902 may include an opening or hole that can be optionally formed in the tibial tray 902 as needed during implantation of the tibial component 900. In certain situations, it may be desirable to remove a portion of the bone to insert the support member 904 therein. In those situations, the opening or hole is formed in the tibial tray 902 such that access to the support member 904 is gained to thereby drive the support member 904 into the bone.

The support member 904 is positioned on the inferior side 910 of the tibial tray 902. The support member 904 has a stem portion 920 that extends away from the inferior side 910 along a longitudinal axis L that forms an angle A with a line that is perpendicular to the inferior side 910 of the tibial tray 902. The angle A is between about 15 degrees and about 45 degrees. In one form the angle A is about 30 degrees. The rotation or angle A of the stem portion 920 enables a better fit for the stem portion 920 in the proximal tibial metaphysis and medullary canal. Often the proximal tibial metaphysis and medullary canal are rotated about 30 degrees, therefore the angle A substantially matches the angle of the proximal tibial metaphysis and medullary canal to provide a better fit of the support member 904 and the tibial tray 902. The stem portion 920 includes a first portion 922 adjacent the inferior side 910 of the tibial tray 902 and a second portion 924 that extends away from the first portion 922. The first portion 922 has a first cross sectional area and the second portion 924 has a second cross sectional area wherein the first cross sectional area is larger than the second cross sectional area in the illustrated embodiment. The first portion 922 has an oval, a teardrop, or a pear cross sectional shape. Beneficially, the unique cross sectional shape of the first portion 922 adds fixation surface area and fits in the proximal tibia better than a stem having a circular cross sectional area. The first portion 922 also includes a plurality of flutes or corrugations 925 that extend longitudinally. The second portion 924 tapers from the first portion 922 to a tip 926 and has a substantially smooth outer surface. Beneficially, the unique configuration of the stem portion 920 provides better rotational stability and liftoff resistance of the tibial tray 902 from bone after implantation. Beneficially, the unique configuration of the stem portion 920 is beneficial for patients with high BMI or Body Mass Index.

Turning now to FIGS. 27-29, a tibial component 1000 is illustrated and includes certain features which correspond to those described above in connection with the tibial component 100 illustrated in FIGS. 1-4. Unless indicated otherwise, similar reference characters are used to indicate similar elements and features. For example, the tibial component 1000 includes a tibial tray 1002, a support member 1004, a first arm 1034, and a second arm 1036, which respectively correspond to the tibial tray 102, the support member 104, the first arm 134, and the second arm 136 as described above. In the interest of conciseness, the following description focuses primarily on features of the tibial component 1000 which may not necessarily have been described above with reference to the tibial component 100.

The support member 1004 is positioned on the inferior side 1010 of the tibial tray 1002. The support member 1004 has a stem portion 1020 that extends away from the inferior side 1010 along a longitudinal axis L. The stem portion 1020 includes a first portion 1022 adjacent the inferior side 1010 of the tibial tray 1002 and a second portion 1024 that extends away from the first portion 1022. The first portion 1022 has a first cross sectional area and the second portion 1024 has a second cross sectional area wherein the first cross sectional area is larger than the second cross sectional area in the illustrated embodiment. The first portion 1022 has an oval, a teardrop, or a pear cross sectional shape and includes a plurality of flutes or corrugations 1025 that extend longitudinally along the length of the first portion 1022. The first portion 1022 has a shorter length than the first portion 922 from the previous embodiment. In the illustrated embodiment, the length of the first portion 922 ranges from about one-quarter to three-quarters of the overall length of the support member 1004. The first portion 1022 also includes a transition portion 1027. The transition portion 1027 tapers from the first portion 1022 to the second portion 1024. In the illustrated form, the transition portion 1027 has a V shape including a first face 1029 that intersects a second face 1031 at the junction of the first portion 1022 and the second portion 1024. The first face 1029 and the second face 1031 are substantially smooth and without flutes or corrugations. In other forms, the first face 1029 and the second face 1031 can include surface irregularities, flutes, or corrugations. The second portion 1024 extends from the transition portion 1027 of the first portion 1022 to a tip 1026. The second portion 1024 has a cross sectional shape of a square with rounded edges and corners or a curvilinear square. In other forms, the second portion 1024 can have a different cross sectional shape. Beneficially, the unique cross sectional shape and length of the first portion 1022 and the second portion 1024 allows for more flexibility of rotational positioning intraoperatively in bone and adds a safety factor when leaving more space between the support member 1004 and the internal surface of the cortical shell when implanted.

The support member 1004 includes a first arm 1034 angled relative to a second arm 1036 mounted on the inferior side 1010 of the tibial tray 1002. The first arm 1034 and the second arm 1036 can be attached to or monolithic with the support member 1004. The first arm 1034 is angled relative to the second arm 1036, but in other embodiments the first and second arms 1034 and 1036 are substantially aligned with one another. The angle between the first arm 1034 and the second arm 1036 can range from about 10 degrees to about 180 degrees. In the illustrated embodiment, the first arm 1034 and the second arm 1036 each have a triangular shape with rounded corners that contact the inferior side 1010 of the tibial tray 1002. The first arm 1034 and the second arm 1036 are substantially flat. The first arm 1034 and the second arm 1036 have a length that extends towards a rim or periphery edge 1040 of the tibial tray 102, however, the second arm 1036 has a longer length than the first arm 1034. The first and second arms 1034 and 1036 each have a sharp edge 1042 and 1044, respectively. The first and second arms 1034 and 1036 assist with rotational stability of the tibial tray 1002 in bone upon implantation.

Turning now to FIGS. 30-32, a tibial component 1100 is illustrated and includes certain features which correspond to those described above in connection with the tibial component 100 illustrated in FIGS. 1-4. Unless indicated otherwise, similar reference characters are used to indicate similar elements and features. For example, the tibial component 1100 includes a tibial tray 1102, a support member 1104, a first peg 1106, and a second peg 1108 which respectively correspond to the tibial tray 102, the support member 104, the first peg 106, and the second peg 108 as described above. In the interest of conciseness, the following description focuses primarily on features of the tibial component 1100 which may not necessarily have been described above with reference to the tibial component 100.

The support member 1104 is positioned on the inferior side 1110 of the tibial tray 1102. The support member 1104 has a stem portion 1120 that extends away from the inferior side 1110 along a longitudinal axis L. In the illustrated embodiment, the longitudinal axis L is substantially perpendicular to the inferior side 1110 of the tibial tray 1102 however the longitudinal axis L can be non-perpendicular in other forms. The stem portion 1120 has a constant cross sectional area along a length thereof to a tip portion 1126 that tapers to a rounded or curved end. The cross sectional area of the stem portion 1120 forms a fluted or cruciform cross sectional shape with four concavely curved walls 1177 that terminate in four leg portions 1179 wherein the curved walls 1177 and the leg portions 1179 are arranged in an alternating relationship in the illustrated embodiment. The four leg portions 1179 extend towards the rim 1140.

The support member 1104 includes a first fin 1130, a second fin 1180, a third fin 1182, and a fourth fin 1184. In the illustrated form, one of the fins 1130, 1180, 1182, and 1184 aligns with each of the leg portions 1179 of the stem portion 1120. The fins 1130, 1180, 1182, and 1184 have a substantially triangular shape but can be shaped differently in other embodiments. The first fin 1130 includes a concavely curved edge 1185 and the second fin 1180 includes a concavely curved edge 1187 that can be configured to cut through or into tissue or bone. The fins 1130, 1180, 1182, and 1184 are positioned on the inferior side 1110 and extend towards the rim or periphery edge 1140 of the tibial tray 1102. As illustrated, the tibial tray 1102 has a kidney-like shape and the fins 1130, 1180, 1182, and 1184 extend to different lengths as measured along the inferior side 1110. The first fin 1130 and the second fin 1180 have a longer length as compared to the third fin 1182 and the fourth fin 1184 as measured along the inferior side 1110. The first fin 1130 and the second fin 1180 have a greater height as compared to the third fin 1182 and the fourth fin 1184 as measured along the longitudinal axis L. In other embodiments, the support member 1104 can include a greater or lesser number of fins 1130, 1180, 1182, and 1184. Moreover, in other forms, the fins 1130, 1180, 1182, and 1184 can be spaced equally from each other or in another arrangement as desired. The third fin 1182 receives the most fixation distally and the fourth fin 1184 receives the most fixation proximally upon implantation of the tibial component 1100. The first fin 1130 and the second fin 1180 are configured to provide strength near the bottom of the tibial tray 1102 and the posterior notch 116. The first fin 1130 and the second fin 1180 are configured to provide for greater fixation for twisting and tilting of the tibial component 1100 upon implantation.

The fins 1130, 1180, 1182, and 1184 include a plurality of rail protrusions or ridges 1186 that extend along the height or a portion of the fins 1130, 1180, 1182, and 1184 as measured along the longitudinal axis L. The plurality of rail protrusions or ridges 1186 have a square or semi square cross sectional shape however in other forms the shape may be rectangular or semi-circular. The plurality of rail protrusions or ridges 1186 have a square or semi square cross sectional shape however in other forms the shape may be rectangular or semi-circular. The plurality of rail protrusions or ridges 1186 can have a variable height and a variable width such that one or more of the plurality of ridges 1186 has a unique height and width. For example, in some forms, the height and width of the plurality of ridges 1186 can range between 1 and 3 millimeters. The plurality of ridges 1186 can be spaced along the fins 1130, 1180, 1182, and 1184 in a uniform spacing arrangement or non-uniform spacing arrangement. The plurality of rail protrusions or ridges 1186 assist with added bone compression and fixation strength of the tibial component 1100 in bone. As can be appreciated, the ridges 1186 can be placed on any embodiment described herein.

Turning now to FIGS. 33-35, a tibial component 1200 is illustrated and includes certain features which correspond to those described above in connection with the tibial component 100 illustrated in FIGS. 1-4. Unless indicated otherwise, similar reference characters are used to indicate similar elements and features. For example, the tibial component 1200 includes a tibial tray 1202, a support member 1204, a first peg 1206, and a second peg 1208 which respectively correspond to the tibial tray 102, the support member 104, the first peg 106, and the second peg 108 as described above. In the interest of conciseness, the following description focuses primarily on features of the tibial component 1200 which may not necessarily have been described above with reference to the tibial component 100.

The support member 1204 is positioned on the inferior side 1210 of the tibial tray 1202. The support member 1204 has a stem portion 1220 that extends away from the inferior side 1210 along a longitudinal axis L. In the illustrated embodiment, the longitudinal axis L is substantially perpendicular to the inferior side 1210 of the tibial tray 1202 however the longitudinal axis L can be non-perpendicular in other forms. The stem portion 1220 has a cross sectional area along a length thereof to a tip portion 1226 that tapers to a rounded end. The cross sectional area of the stem portion 1220 forms a six pointed star shape with six concavely curved walls 1277 that terminate in six leg portions 1279 wherein the curved walls 1277 and the leg portions 1279 are arranged in an alternating relationship and extend about two-thirds of the length of the stem portion 1220 in the illustrated embodiment. Between each of the concavely curved walls 1277 is a channel 1281 that extends from the inferior side 1210 to the tip portion 1226. The leg portions 1279 extend towards the rim 1240.

The support member 1204 includes a first fin 1130 and a second fin 1180. In the illustrated form, first fin 1230 aligns with one of the leg portions 1279 and the second fin 1180 aligns with another of the leg portions 1279 of the stem portion 1220. The fins 1230 and 1280 have a substantially triangular shape but can be shaped differently in other embodiments. The fins 1230 and 1280 are positioned on the inferior side 1210 and extend towards the rim or periphery edge 1240 of the tibial tray 1202. As illustrated, the tibial tray 1202 has a kidney-like shape and the fins 1230 and 1280 extend to different lengths as measured along the inferior side 1210. The first fin 1230 has a shorter length than the second fin 1280 as measured along the inferior side 1210. In other embodiments, the support member 1204 can include a greater or lesser number of fins 1230 or 1280. Moreover, in other forms, the fins 1230 and 1280 can be spaced in another arrangement as desired. The fins 1230 and 1280 include a plurality of rail protrusions or ridges 1286 that extend along the height or a portion of the fins 1230 and 1280 as measured along the longitudinal axis L.

The tibial component 1200 provides rotational stability at the bone resection surface and through the majority of the penetrated length of the patient. The rounded tip portion 1226 of the stem portion 1220 allows for flexibility and placement intraoperatively.

Turning now to FIG. 36, a tibial component 1300 is illustrated and includes certain features which correspond to those described above in connection with the tibial component 1100 illustrated in FIGS. 30-32. Unless indicated otherwise, similar reference characters are used to indicate similar elements and features. For example, the tibial component 1300 includes a tibial tray 1302, a first support member 1304, a first peg 1306, and a second peg 1308 which respectively correspond to the tibial tray 1102, the support member 1104, the first peg 1106, and the second peg 1108 as described above. In the interest of conciseness, the following description focuses primarily on features of the tibial component 1300 which may not necessarily have been described above with reference tibial component 1100. The tibial component 1300 may have features that are different in the medial and lateral directions. The tibial component 1300 may utilize all of the features described in the application including fins, stems, arms, protrusions, ribs, and notches.

In addition to the first support member 1304, a second support member 1305 is also positioned on the inferior side 1310 of the tibial tray 1302. The first support member 1304 has a first stem portion 1320 that extends away from the inferior side 1310 and the second support member 1305 has a second stem portion 1321 that extends away from the inferior side 1310 of the tibial tray 1302. The first stem portion 1320 and the second stem portion 1321 may be connected with a connecting member 1333 as illustrated or separate elements without the presence of the connecting member 1333. The cross sectional areas of the first stem portion 1320 and the second stem portion 1321 each form a fluted or cruciform cross section shape with one or more concavely curved walls that terminate in leg portions wherein the curved walls and the leg portions are arranged in an alternating relationship in the illustrated embodiment. The leg portions extend towards the rim.

The first support member 1304 includes one or more fins 1330 wherein each of the fins 1330 may be different or similar. The second support member 1305 includes one or more fins 1380 wherein each of the fins 1380 may be different or similar. The one or more fins 1330 may be similar or different than the one or more fins 1380. The one or more fins 1330 and/or the one or more fins 1380 may be similar or different than the fins 1130, 1180, 1182, and 1184. As illustrated, the tibial tray 1302 has a kidney-like shape and the fins 1330 and 1380 extend to different lengths as measured along the inferior side 1310. In other embodiments, the first support member 1304 can include a greater or lesser number of fins 1330. Similarly the second support member 1305 can include a greater or lesser number of fins 1380.

The fins 1330 and 1380 and the connecting member 1333 each include one or more rail protrusions or ridges 1386 that extend along the height of the respective element. The rail protrusions or ridges 1386 are similar to rail protrusions or ridges 1186.

The tibial tray 1302 includes a posterior notch 1316 that extends towards the connecting member 1333. The posterior notch 1316 can be sized for preserving one or both of the cruciate ligaments.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A tibial component comprising:
a tibial tray having a superior side, an inferior side, a posterior side, an anterior side, a first side, a second side, and a rim defining a periphery thereof; and
a support member connected to the inferior side of the tibial tray, the support member having a stem portion, the stem portion including a plurality of fins, the plurality of fins including a plurality of fins having a first configuration and a plurality of fins having a second configuration, wherein the plurality of fins having the first configuration have a longer length as compared to the plurality of fins having the second configuration as measured along the inferior side;
wherein the plurality of fins having the first configuration include a first fin and a second fin, the first fin extending from the stem portion toward the rim, the first fin extending posteriorly and toward the first side, the second fin extending from the stem portion toward the rim, the second fin extending posteriorly and toward the second side, each of the first and second fins including a curved profile as they extend from the stem portion towards the first and second sides, respectively, the curved profile bending about an axis that is perpendicular to the superior side; and
wherein the plurality of fins having the second configuration include a third fin and a fourth fin, the third fin extending from the stem portion toward the rim, the third fin extending anteriorly and toward the first side, the fourth fin extending from the stem portion toward the rim, the fourth fin extending anteriorly and toward the second side; the third fin including a length extending from the stem portion towards an anterior edge of the third fin, the fourth fin including a length extending from the stem portion towards an anterior edge of the fourth fin, the length of the fourth fin being greater than the length of the third fin.

2. The tibial component of claim 1, wherein the first, second, third, and fourth fins are spaced equally around the stem portion.

3. The tibial component of claim 1, wherein the stem portion includes a first portion adjacent the inferior side of the tibial tray and a second portion that extends away from the first portion, the first portion has a first cross sectional area and the second portion has a second cross sectional area wherein the first cross sectional area is larger than the second cross sectional area.

4. The tibial component of claim 1, wherein the plurality of fins each include one or more rail protrusions.

5. The tibial component of claim 1, wherein the plurality of fins having the first configuration and the plurality of fins having the second configuration each include a plurality of rail protrusions.

6. The tibial component of claim 5, wherein the plurality of rail protrusions extend along a height of the plurality of fins having the first configuration and the plurality of fins having the second configuration.

7. The tibial component of claim 5, wherein the plurality of rail protrusions are spaced along the plurality of fins having the first configuration and the plurality of fins having the second configuration in a uniform spacing arrangement.

8. The tibial component of claim 5, wherein the plurality of rail protrusions are spaced along the plurality of fins having the first configuration and the plurality of fins having the second configuration in a non-uniform spacing arrangement.

9. The tibial component of claim 1, wherein the plurality of fins have a height that extends from the inferior side of the tibial tray to a location on the stem portion that is between about 0.5 and 0.90 of a height of the stem portion.

10. The tibial component of claim 1, wherein the stem portion includes a groove positioned between the first and second fins and the stem portion includes a groove positioned between the third and fourth fins.

11. The tibial component of claim 1, further comprising: one or more pegs attached to the inferior side of the tibial tray.

12. The tibial component of claim 1, wherein the tibial tray defines a notch.

13. The tibial component of claim 1, wherein the stem portion includes a fluted cross sectional shape with four concavely curved walls that terminate in the first, second, third, and fourth fins.

14. The tibial component of claim 1, wherein the first fin and the second fin each include a concavely curved edge configured to cut into tissue or bone.

15. The tibial component of claim 1, wherein the curved profile of the first and second fins curves toward the anterior side and away from the posterior side.

* * * * *